United States Patent [19]
Yoon

[11] Patent Number: 5,984,933
[45] Date of Patent: *Nov. 16, 1999

[54] APPARATUS FOR SUTURING TISSUE

[76] Inventor: InBae Yoon, 2101 Highland Ridge Dr., Phoenix, Md. 21131

[ * ] Notice: This patent is subject to a terminal disclaimer.

[21] Appl. No.: 08/902,297

[22] Filed: Jul. 29, 1997

Related U.S. Application Data

[63] Continuation of application No. 08/366,285, Dec. 29, 1994, Pat. No. 5,665,109.

[51] Int. Cl.$^6$ .................................................... A61B 17/04
[52] U.S. Cl. ........................... 606/148; 606/224; 606/232
[58] Field of Search ..................................... 606/232, 224, 606/225, 226, 227, 228, 139, 144, 148

[56] References Cited

U.S. PATENT DOCUMENTS

| | | |
|---|---|---|
| 1,852,098 | 4/1932 | Anderson . |
| 2,075,508 | 3/1937 | Davidson . |
| 2,199,025 | 4/1940 | Conn . |
| 3,033,204 | 5/1962 | Wood . |
| 3,541,591 | 11/1970 | Hoegerman . |
| 3,570,497 | 3/1971 | Lemole . |
| 3,580,256 | 5/1971 | Wilkinson et al. ..................... 606/232 |
| 3,625,220 | 12/1971 | Engelsher . |
| 3,664,345 | 5/1972 | Dabbs et al. . |
| 3,753,438 | 8/1973 | Wood et al. . |
| 3,775,825 | 12/1973 | Wood et al. . |
| 3,802,438 | 4/1974 | Wolvek . |
| 3,831,608 | 8/1974 | Kletschka et al. . |
| 3,857,396 | 12/1974 | Hardwick . |
| 3,910,281 | 10/1975 | Kletschka et al. . |
| 3,931,821 | 1/1976 | Kletschka et al. . |
| 3,976,079 | 8/1976 | Samuels et al. . |
| 4,006,747 | 2/1977 | Kronenthal et al. . |
| 4,069,825 | 1/1978 | Akiyama . |
| 4,235,238 | 11/1980 | Ogin et al. . |
| 4,291,698 | 9/1981 | Fuchs et al. . |
| 4,387,489 | 6/1983 | Dudek . |
| 4,440,171 | 4/1984 | Nomoto et al. . |
| 4,669,473 | 6/1987 | Richards et al. . |
| 4,750,492 | 6/1988 | Jacobs . |
| 4,901,721 | 2/1990 | Hakki ....................... 606/232 |
| 4,932,962 | 6/1990 | Yoon et al. . |
| 4,935,027 | 6/1990 | Yoon . |
| 4,950,285 | 8/1990 | Wilk . |
| 4,969,892 | 11/1990 | Burton et al. . |
| 4,982,149 | 1/1991 | Yoon et al. . |
| 5,009,663 | 4/1991 | Broome . |
| 5,037,433 | 8/1991 | Wilk et al. . |
| 5,053,047 | 10/1991 | Yoon . |
| 5,074,874 | 12/1991 | Yoon et al. .............................. 606/224 |
| 5,078,731 | 1/1992 | Hayhurst . |
| 5,100,418 | 3/1992 | Yoon et al. . |
| 5,123,913 | 6/1992 | Wilk et al. . |
| 5,129,912 | 7/1992 | Noda et al. . |
| 5,152,769 | 10/1992 | Baber . |
| 5,160,339 | 11/1992 | Chen et al. . |
| 5,171,251 | 12/1992 | Bregen et al. . |
| 5,178,629 | 1/1993 | Kammerer .............................. 606/224 |
| 5,207,693 | 5/1993 | Phillips . |
| 5,207,694 | 5/1993 | Broome . |
| 5,211,650 | 5/1993 | Noda . |
| 5,222,976 | 6/1993 | Yoon . |
| 5,234,449 | 8/1993 | Bruker et al. . |
| 5,269,809 | 12/1993 | Hayhurst et al. . |

(List continued on next page.)

FOREIGN PATENT DOCUMENTS 2651113  9/1991  France .

Primary Examiner—Michael Buiz
Assistant Examiner—Daphna Shai
Attorney, Agent, or Firm—Blank Rome Comisky & McCauley LLP

[57] ABSTRACT

Method and apparatus for suturing and ligating anatomical tissue utilizes one or more knotting elements carried by a length of filamentous suture material for tying the suture material to create one or more adjustably tensioned stitches. The knotting elements are carried by the suture material at fixed spaced positions or can be movable along the suture material, and suture instruments are provided to facilitate the formation of a plurality of stitches, particularly during endoscopic procedures.

2 Claims, 17 Drawing Sheets

U.S. PATENT DOCUMENTS

| | | |
|---|---|---|
| 5,282,809 | 2/1994 | Kammerer et al. . |
| 5,282,832 | 2/1994 | Toso et al. . |
| 5,306,290 | 4/1994 | Martins et al. ......................... 606/232 |
| 5,312,436 | 5/1994 | Coffey et al. . |
| 5,318,578 | 6/1994 | Hasson . |
| 5,320,629 | 6/1994 | Noda et al. . |
| 5,330,442 | 7/1994 | Green et at al. . |
| 5,330,491 | 7/1994 | Walker et al. . |
| 5,330,503 | 7/1994 | Yoon . |
| 5,336,231 | 8/1994 | Adair . |
| 5,354,298 | 10/1994 | Lee et al. . |
| 5,366,459 | 11/1994 | Yoon . |
| 5,368,595 | 11/1994 | Lewis . |
| 5,370,661 | 12/1994 | Branch . |
| 5,376,101 | 12/1994 | Green et al. . |
| 5,383,905 | 1/1995 | Golds et al. . |
| 5,391,173 | 2/1995 | Wilk . |
| 5,454,834 | 10/1995 | Boebel et al. ......................... 606/228 |

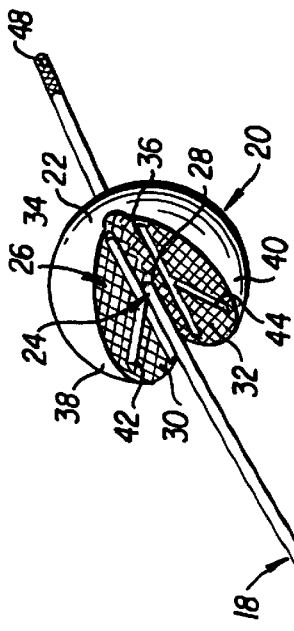
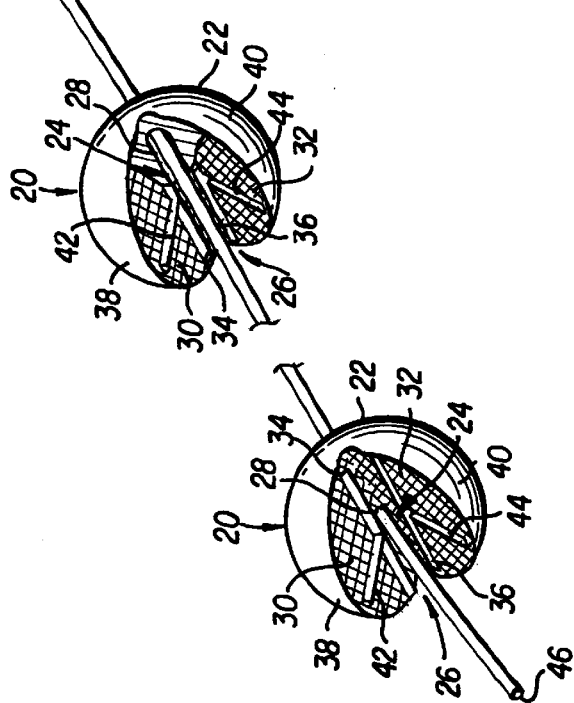

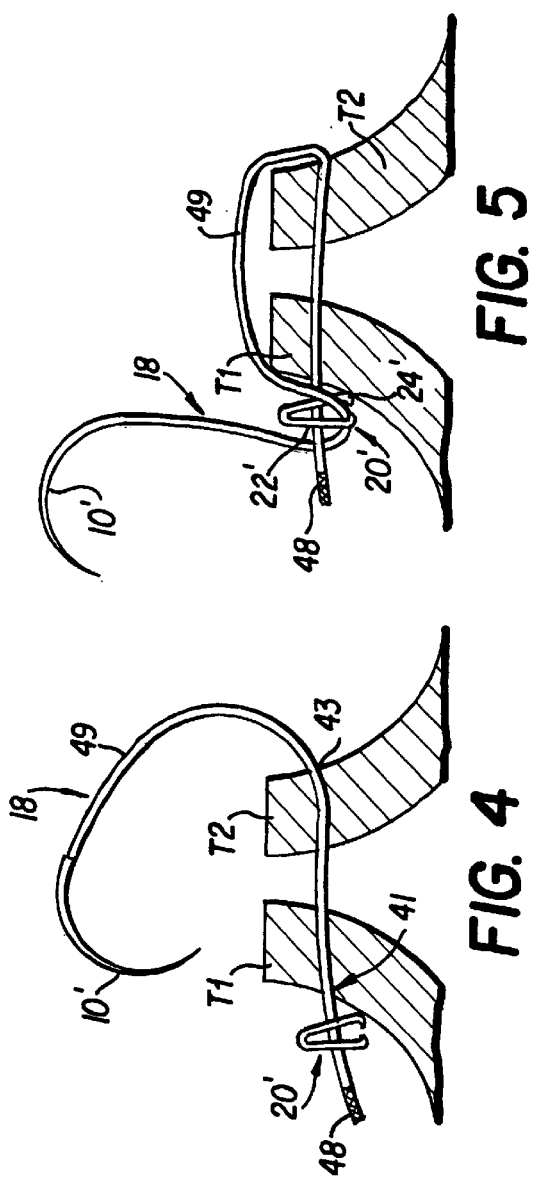
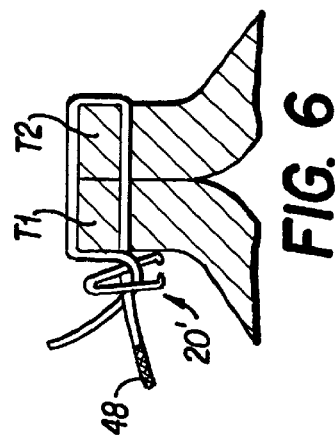
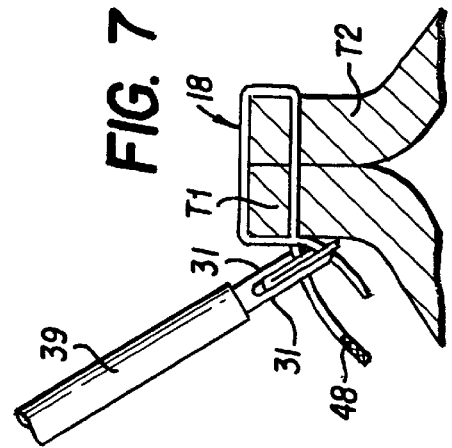
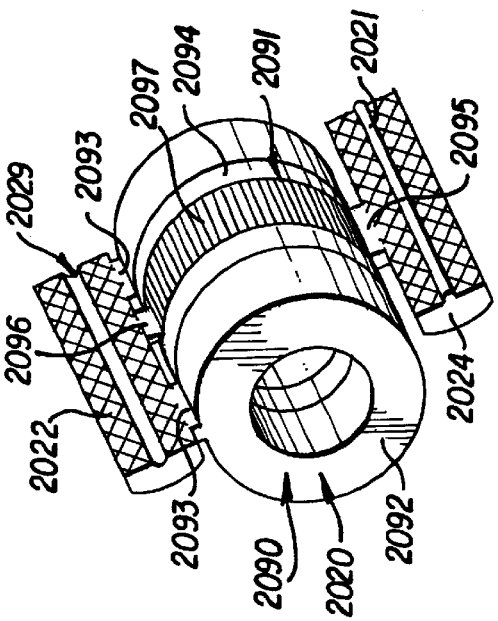
FIG. 6
FIG. 41
FIG. 5
FIG. 4
FIG. 7

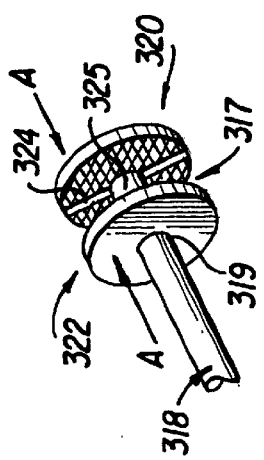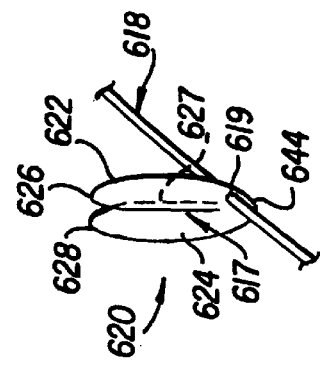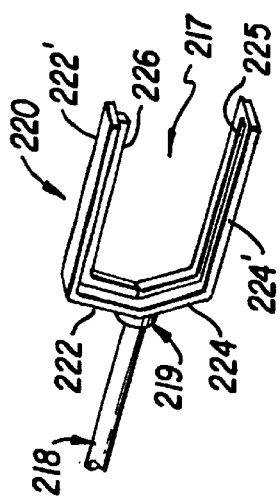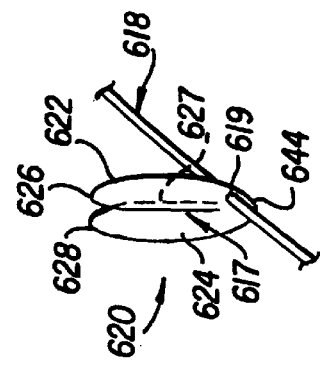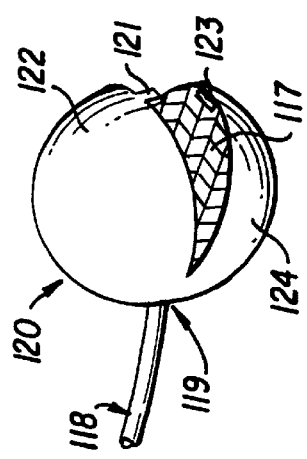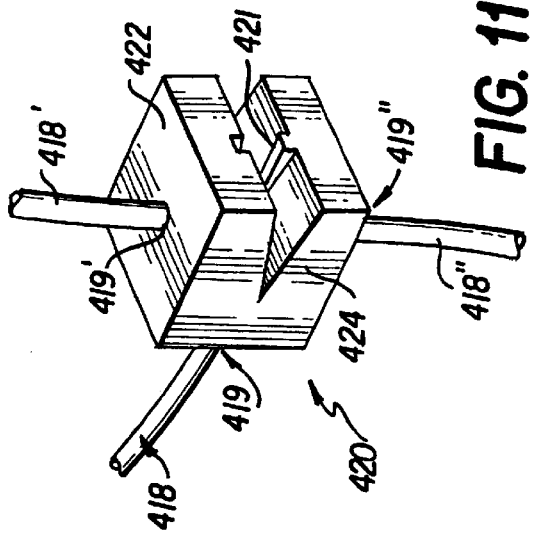

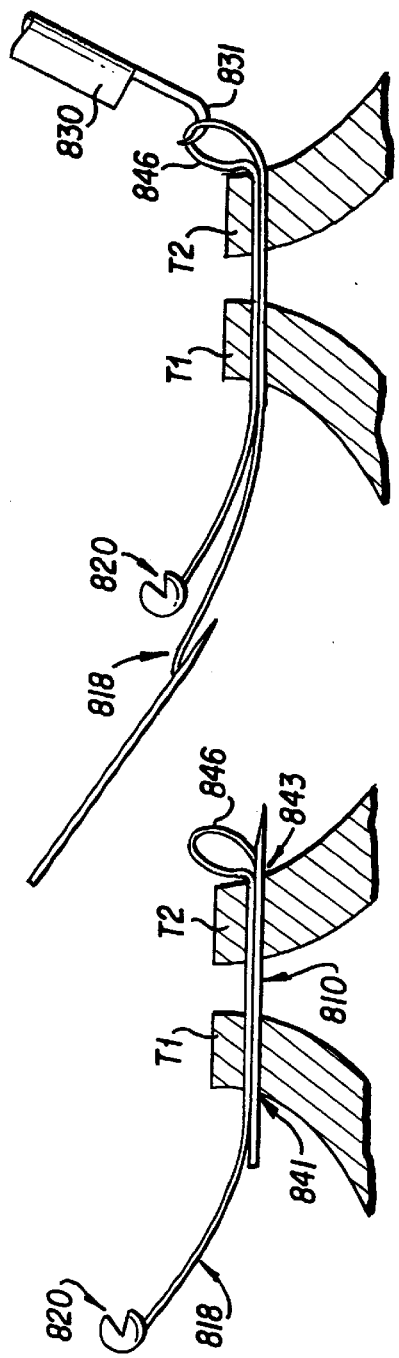
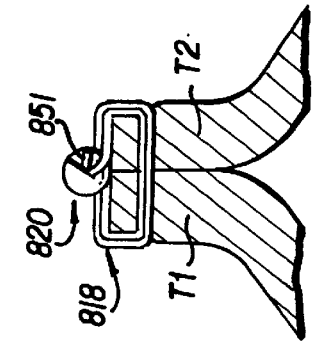
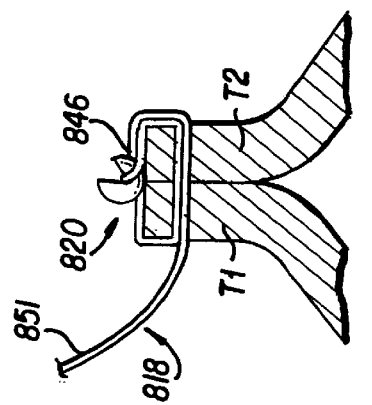
FIG. 17
FIG. 18
FIG. 19
FIG. 20
FIG. 21

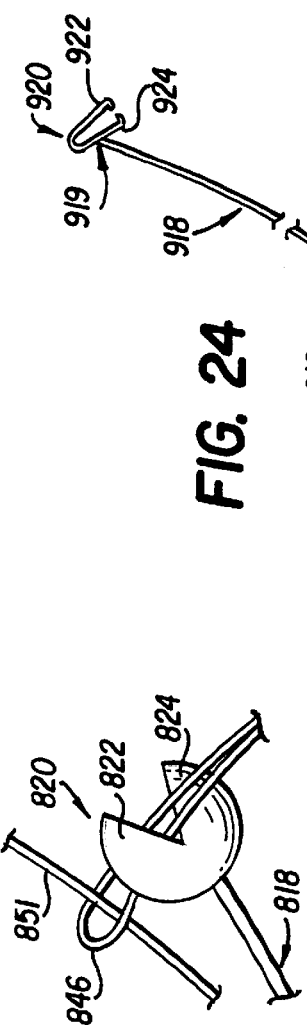
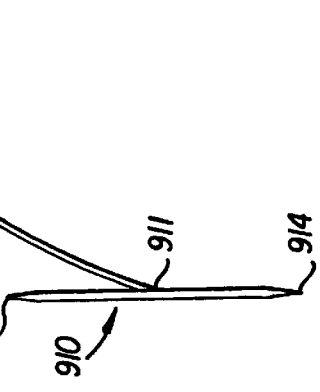
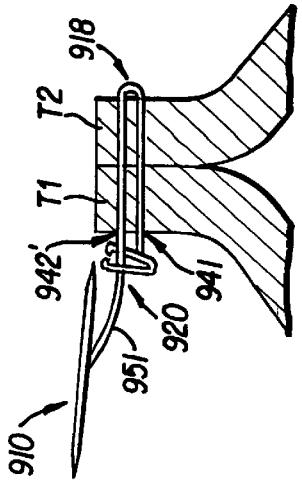
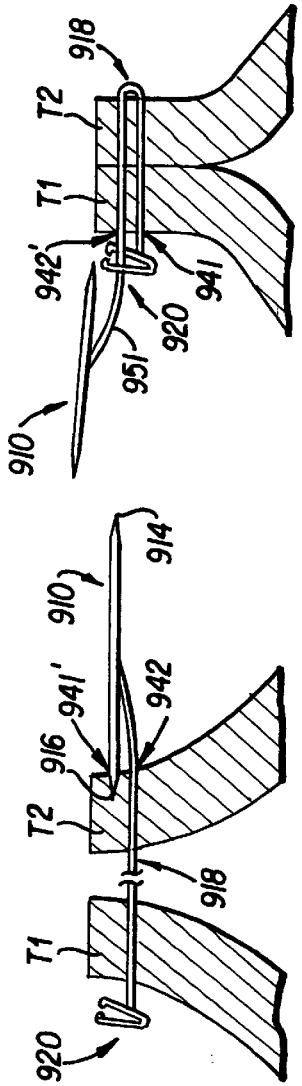
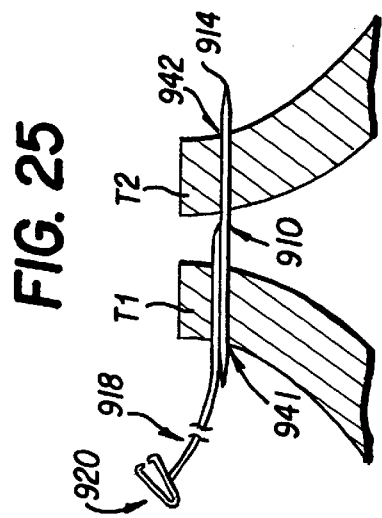

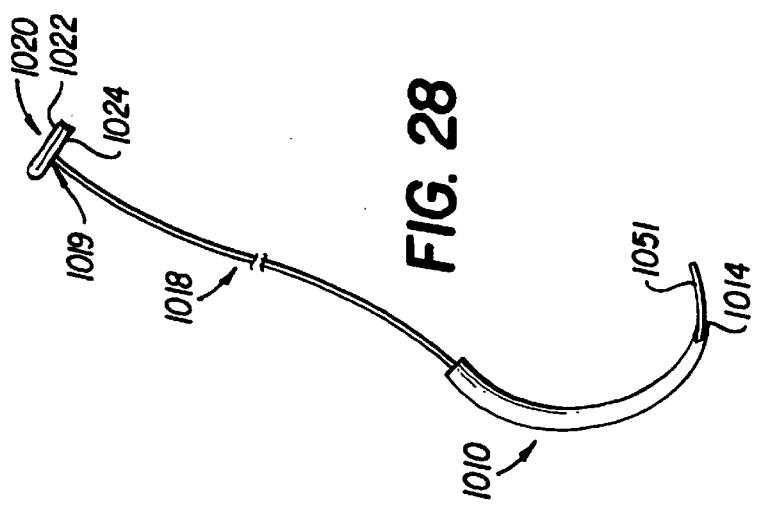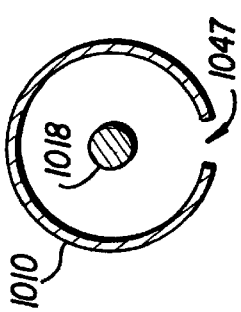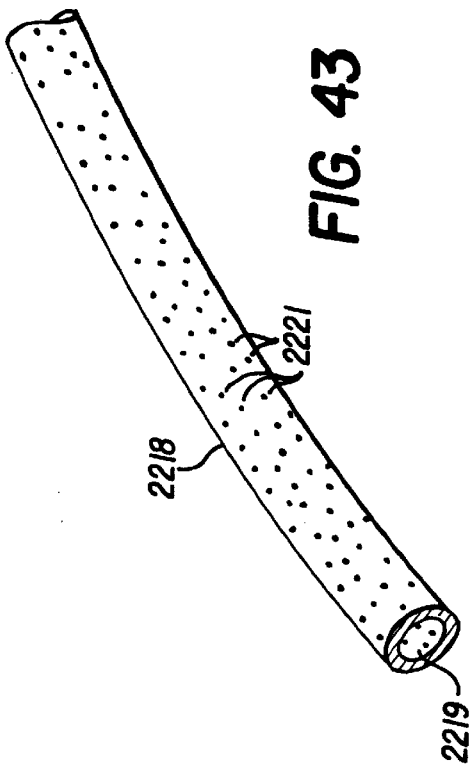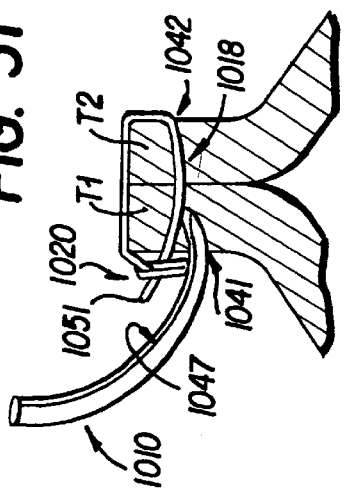

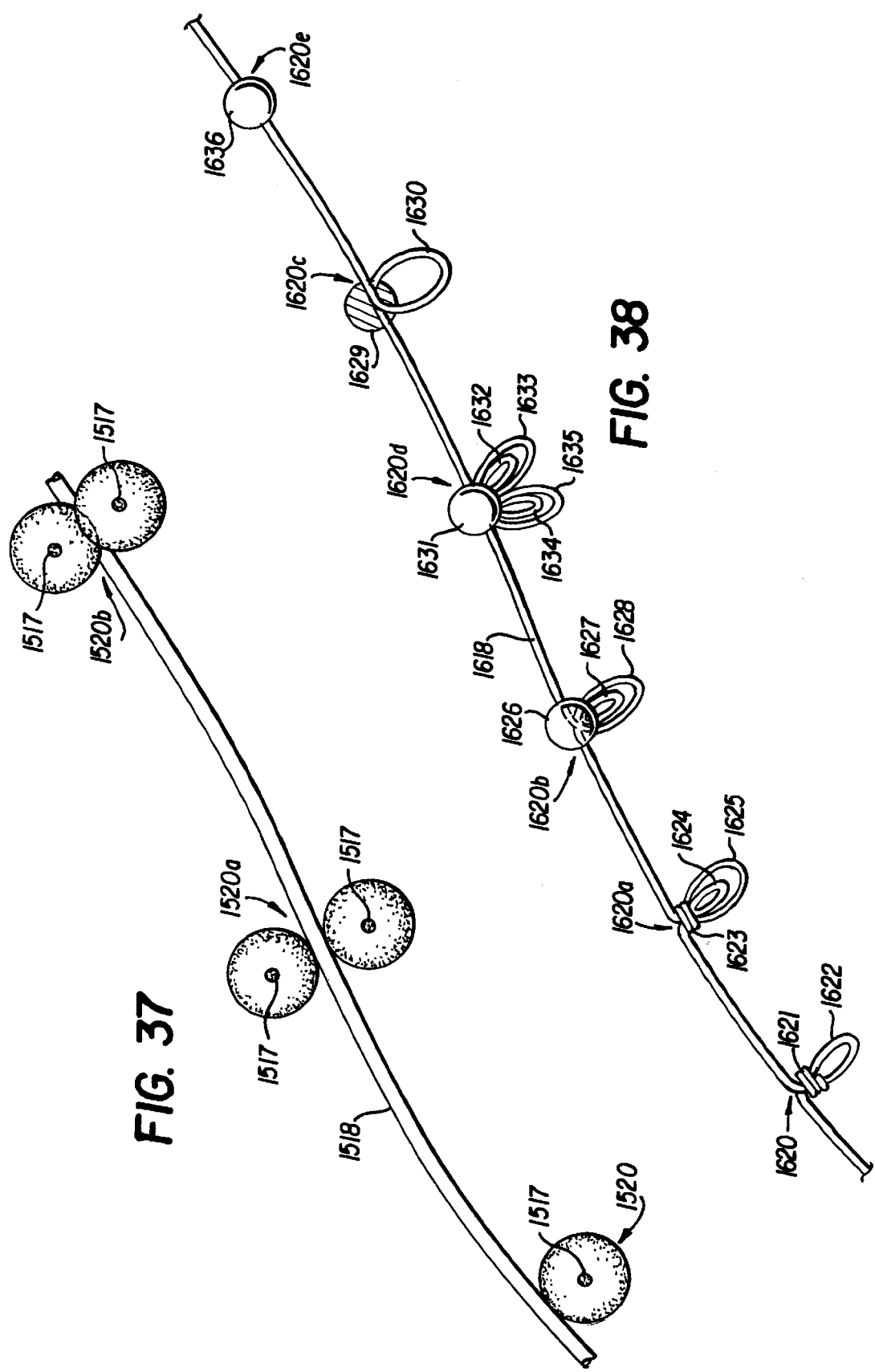

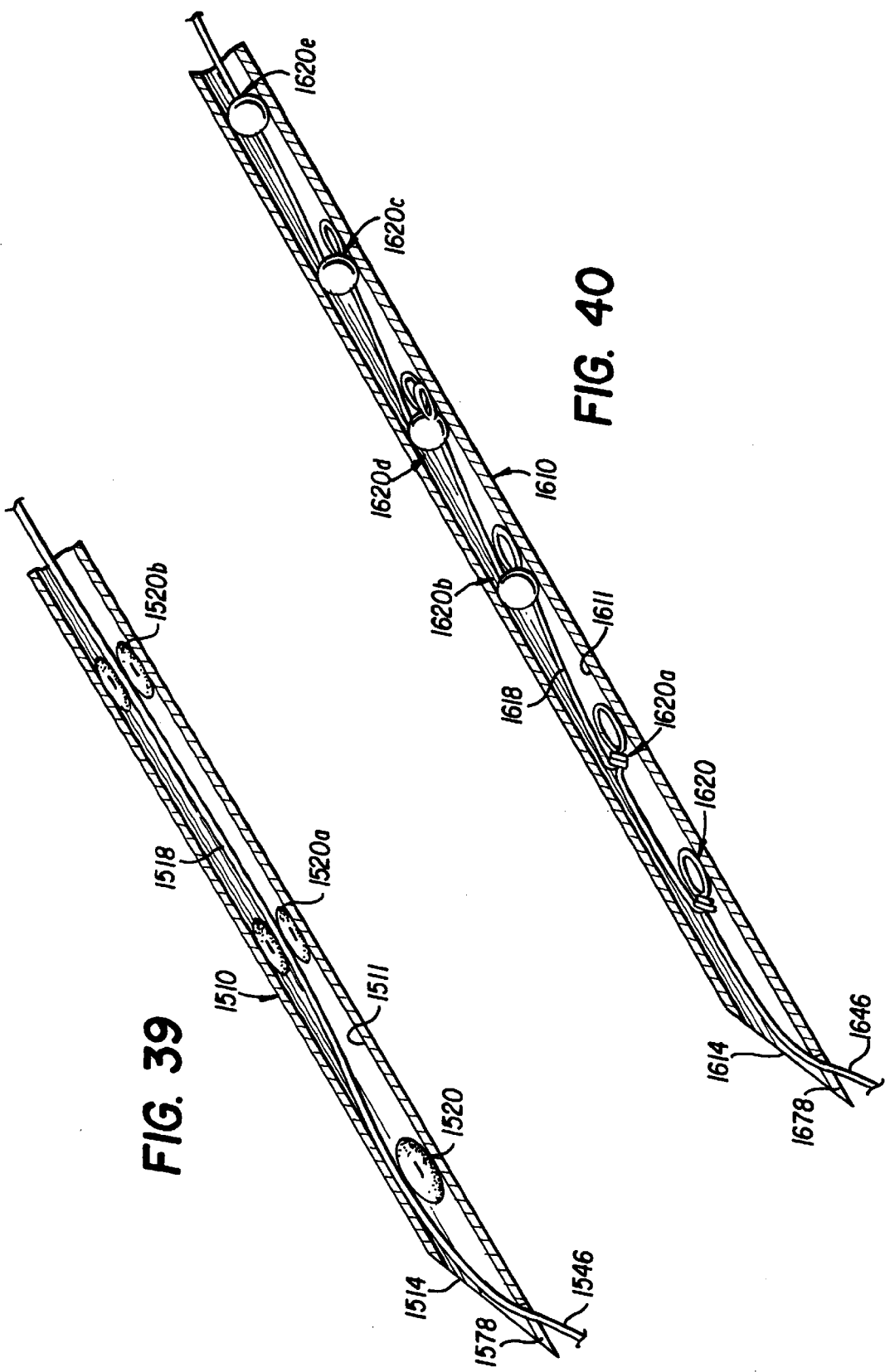

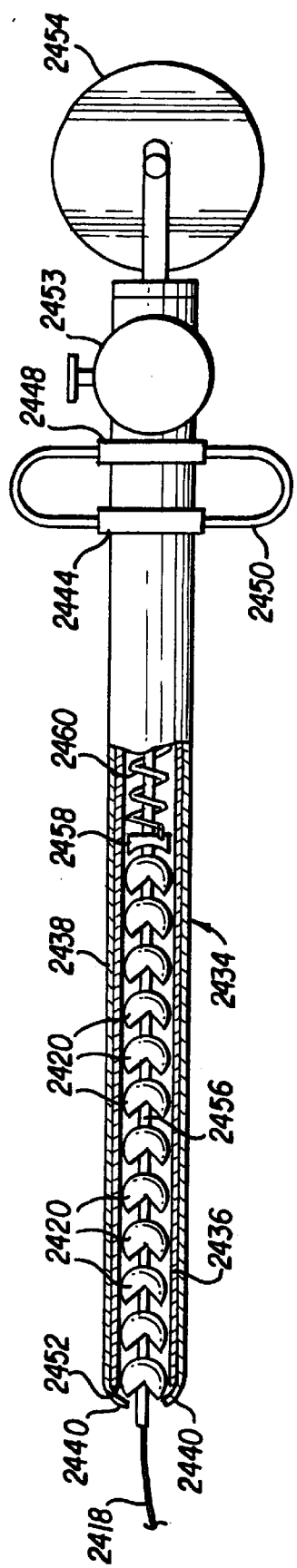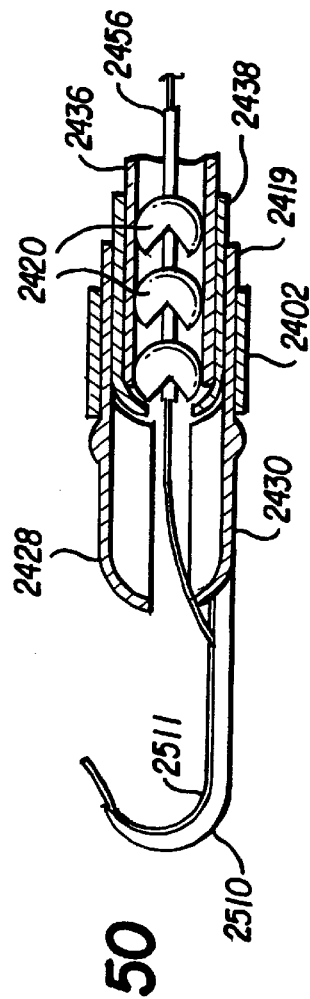
FIG. 49
FIG. 50

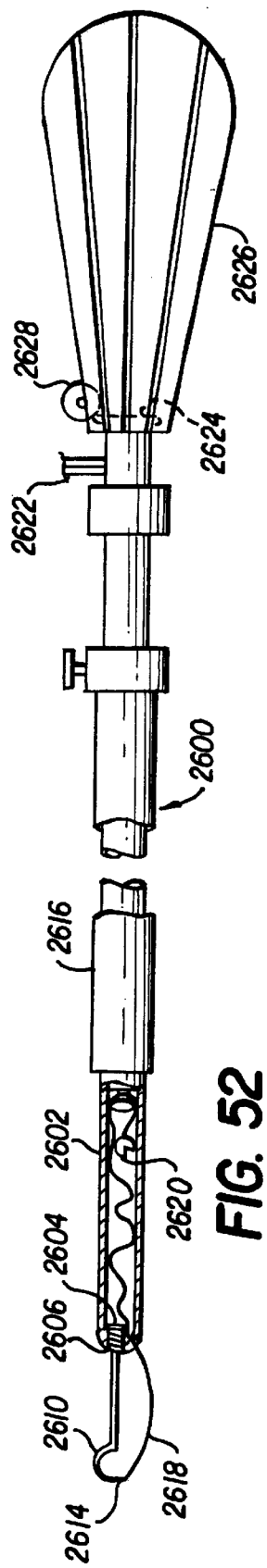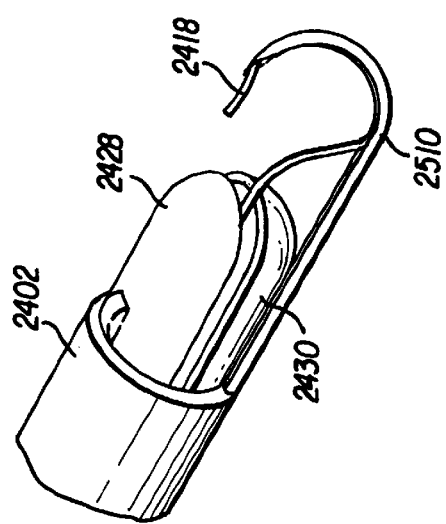
FIG. 52
FIG. 51

APPARATUS FOR SUTURING TISSUE

This application is a Continuation of application Ser. No. 08/366,285, filed Dec. 29, 1994, now U.S. Pat. No. 5,665,109.

BACKGROUND OF THE INVENTION

1. Field of the Invention

The present invention pertains to suturing of bodily tissue and, more particularly, to methods and apparatus for suturing tissue during endoscopic and open surgical procedures.

2. Discussion of the Prior Art

Suturing of bodily tissue is a time consuming part of most surgical procedures including both open surgery and endoscopic or minimally invasive surgery. By open surgery is meant surgery wherein the surgeon gains access to the surgical site via a relatively large incision, and by endoscopic surgery is meant surgery wherein the surgeon gains access to the surgical site via one or more portals through which endoscopes are introduced to view the surgical site and through which various instruments are introduced to the surgical site. There are many common endoscopic surgical procedures, including arthroscopy, laparoscopy (pelviscopy), gastroentroscopy and laryngobronchoscopy, for example. In the past, suturing has been accomplished with the use of a sharp metal suture needle attached to the end of a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed; however, knotting of the suture material is time consuming and tedious work, particularly in microsurgery and endoscopic surgery. In microsurgery, suturing is necessarily time consuming due to the limited space at the suture site, the small size of the suture needle and the suture material and the concomitant difficult manipulation required to pass the suture needle through the tissue and to tie a knot in the suture material. With respect to endoscopic surgery, suturing and tying knots represents an even more time consuming procedure due to the difficult maneuvers required. Accordingly, while endoscopic surgery would be preferred for most procedures, the advantages can be outweighed by the disadvantages caused by the length of time required to complete the endoscopic surgical procedure, which time is greatly extended due to the time required for suturing. It is extremely important for knotting or tying of sutures to be consistently performed to provide a stitch with controlled, non-slipping, tension; and, to this end, it is common for surgeons to tie double knots, that is, a first knot to control tension and a second knot to secure the first knot. Accordingly, it will be appreciated that there is a great need for improving the tying procedure involved in suturing to permit expedited knotting while also providing consistent, secure knots.

There have been many attempts to provide devices to take the place of conventional suturing with a suture needle and a length of suture material; however, such devices have essentially been staples, clips or clamps not facilitating adjustment of tension by the surgeon. French Patent No. 2,651,113 to Alain and U.S. Pat. No. 3,123,077 to Alcamo, U.S. Pat. No. 3,570,497 to Lemole, U.S. Pat. No. 4,548,202 to Duncan, U.S. Pat. No. 4,592,355 to Antebi, U.S. Pat. No. 4,730,615 to Sutherland et al, U.S. Pat. No. 4,935,028 to Drews, U.S. Pat. No. 4,950,285 to Wilk, U.S. Pat. No. 4,955,913 to Robinson and U.S. Pat. No. 5,123,913 to Wilk are representative of devices for use during open surgery to adjustably hold tissue together similar to suturing and tying but fail to provide the same feel and tension control as tying or knotting a length of suture material. U.S. Pat. No. 3,910,281 to Kletschka et al is representative of suture anchors for facilitating tying. U.S. Pat. No. 2,075,508 to Davidson, U.S. Pat. No. 2,199,025 to Conn and U.S. Pat. No. 3,664,345 to Dabbs et al are illustrative of suture buttons for retaining sutures. U.S. Pat. No. 3,976,079 to Samuels et al and U.S. Pat. No. 4,291,698 to Fuchs, deceased, et al, are representative of suture buttons having structure for clamping suture material. U.S. Pat. No. 4,750,492 to Jacobs discloses apparatus and method for suturing utilizing both an anchor and a clenching device.

Endoscopic surgery is preferred over open surgery due to the greatly reduced trauma and wound healing time for the patient and due to concomitant cost savings associated with shorter hospital stays and performing surgery in non-hospital or out-patient surgery sites. Accordingly, there has been much effort spent to develop techniques for facilitating the suturing normally performed by use of a suture needle and a length of suture material. Alternative techniques proposed have included electrical coagulation, mechanical devices such as clips, clamps and staples, and lasers; however, no alternative technique has yet been well accepted by surgeons to produce the results obtained by suturing and tying. Thus, there is a great need for suturing techniques useful in endoscopic surgery to permit surgeons to suture with controlled tension and approximation of tissue similar to that obtained by conventional knot tying.

U.S. Pat. No. 3,541,591 to Hoegerman, U.S. Pat. No. 3,753,438 to Wood et al, and U.S. Pat. No. 3,775,825 to Wood et al disclose apparatus and methods for suturing wherein clips are secured on the free ends of a suture filament. U.S. Pat. No. 5,078,731 to Hayhurst, U.S. Pat. No. 5,160,339 to Chen et al, U.S. Pat. No. 5,171,251 to Bregen et al, U.S. Pat. No. 5,234,449 to Bruker et al, U.S. Pat. No. 5,181,832 to Toso et al and U.S. Pat. No. 5,330,442 to Green et al are representative of clips for clamping suture material to eliminate knotting during endoscopic procedures. European Patent Publication No. 0.477,020A to Chen et al and U.S. Pat. No. 5,015,250 to Foster, U.S. Pat. No. 5,037,433 to Wilk et al, U.S. Pat. No. 5,059,201 to Asnis, U.S. Pat. No. 5,084,058 to Li, U.S. Pat. No. 5,087,263 to Li, U.S. Pat. No. 5,100,415 to Hayhurst, U.S. Pat. No. 5,100,421 to Christoudias, U.S. Pat. No. 5,144,961 to Chen, U.S. Pat. No. 5,147,373 to Ferzli, U.S. Pat. No. 5,152,769 to Baber and U.S. Pat. No. 5,163,946 to Li are representative of needle holders and apparatus for suturing, knotting or ligating during endoscopic procedures. The above techniques and instruments have the disadvantages of requiring complex instruments, of requiring special suture devices, of being difficult to manipulate and/or of not sufficiently reducing the time required for suturing and tying or knotting.

U.S. Pat. No. 4,932,962, U.S. Pat. No. 4,981,149, U.S. Pat. No. 5,074,874 and U.S. Pat. No. 5,100,418 to Yoon et al and U.S. Pat. No. 4,935,027, U.S. Pat. No. 5,053,047, U.S. Pat. No. 5,222,076, U.S. Pat. No. 5,330,503 and U.S. Pat. No. 5,336,459 to Yoon disclose methods and apparatus particularly useful for suturing during endoscopic procedures to permit tissue approximation with controlled tension.

SUMMARY OF THE INVENTION

Accordingly, it is a primary object of the present invention to provide apparatus and methods for suturing anatomical or bodily tissue in a time efficient, consistent and precise manner.

Another object of the present invention is to utilize a single, plastically deformable knotting element to form a knot between opposite ends of a stitch of filamentous suture material and, further, to use a plurality of such knotting elements with a single length of filamentous suture material to form a plurality of stitches in tissue in an expeditious manner.

An additional object of the present invention is to form a plurality of stitches in tissue using a hollow suturing instrument accommodating a plurality of knotting elements carried by a length of filamentous suture material.

A further object of the present invention is to suture anatomical tissue utilizing a suturing apparatus including a needle, a length of filamentous suture material secured to the needle and at least one knotting element having an attachment site secured to a first segment of the suture material and a grasping site including opposed surfaces having a first position for receiving a second segment of the suture material and a second position to grasp the second segment of the suture material to effect a knot to form a suture stitch in the anatomical tissue.

The present invention has another object in that a plurality of knotting elements are arranged in series along a length of suture material, each of the knotting elements including a site for engaging a first segment of the suture material and a site for engaging a second segment of the suture material.

An additional object of the present invention is to secure a plurality of knotting elements at spaced positions along a length of suture material to define stitch segments between two knotting elements with the knotting elements acting as knots for the stitch segments when the stitch segments are passed through or around anatomical tissue and back to the knotting elements.

It is also an object of the present invention to suture anatomical tissue utilizing a hollow needle and a suture supply including a length of suture material movable through the hollow needle and a plurality of knotting elements movable internally or externally along the needle.

The present invention has as a further object to suture anatomical tissue by moving a hollow needle forwardly through the tissue from an entry point to an exit point to position a segment of a length of suture material received in the needle at the exit point, moving the needle rearwardly and out of the entry point to withdraw the needle from the tissue, pulling the suture material forwardly through the tissue to cause a distalmost one of a plurality of knotting elements carried by the suture material to be positioned adjacent the tissue at the entry point, engaging the segment of suture material with the distalmost knotting element to knot a stitch segment to form a first stitch and cutting the suture material proximally of the distalmost knotting element to define a new segment for the suture material and a new distalmost knotting element for forming a second stitch. Additional stitches, as required, are formed in the same manner.

Some of the advantages of the present invention are that controlled tissue approximation can be achieved to provide a "feel" similar to suturing with knot tying in an expeditious manner for use in open or endoscopic procedures, the variety of surgical procedures that can be performed endoscopically without increasing the time required for suturing is expanded, suturing can be accomplished using standard filamentous suture materials, suturing can be accomplished using standard, available instruments or specially designed instruments of simple construction allowing the instruments to be disposable or easily sterilizable for reuse, a plurality of stitches can be formed without having to withdraw instruments from the body after completion of each stitch as is particularly advantageous for endoscopic use, the size of the stitch segments can be selectively adjusted during use, enhanced securement of suture stitches is realized to ensure that completed stitches remain intact, the knotting elements can be optimally oriented to engage the suture material for certain procedures and the amount of space required for suturing is minimized.

These and other objects, advantages and benefits are realized with the present invention as generally characterized in a suturing apparatus including a length of filamentous suture material having an end received by a needle and a knotting element having an attachment site secured to a first segment of the suture material and a grasping site including a pair of opposed surfaces for grasping a second segment of the suture material, the opposed surfaces being movable to non-releasably grasp the second segment of the suture material to effect a knot between the first and second segments of the suture material. The present invention is further generally characterized in a suture supply including a length of filamentous suture material and a plurality of knotting elements each having an attachment site for receiving a segment of the suture material and a grasping site for grasping another segment of the suture material with the knotting elements being arranged in series along the suture material. The present invention is additionally generally characterized in a suture supply including a length of suture material and a plurality of knotting elements secured to the suture material at spaced positions to define stitch segments between two of the knotting elements with the knotting elements including means for selectively engaging the suture material to act as a knot for the stitch segments. A suturing apparatus in accordance with the present invention is generally characterized in a hollow needle having a lumen and a sharp distal end for penetrating tissue, a length of suture material received in the needle and a plurality of knotting elements carried by the suture material at spaced positions to define stitch segments between the knotting elements with the knotting elements having grasping sites for grasping a segment of the suture material to effect a knot for the stitch segments and the knotting elements being initially disposed proximally of the needle distal end and being positionable individually beyond the needle distal end.

The present invention is also generally characterized in a method of suturing tissue including the steps of providing a length of filamentous suture material carrying a knotting element and a needle coupled with the suture material, penetrating the tissue with the needle from an entry point to an exit point to pass a portion of the suture material through the tissue to be accessible at the exit point, moving the suture material to be received in the knotting element to form a stitch segment extending from the knotting element through the tissue and back to the knotting element, tightening the stitch segment to a desired tension and plastically deforming the knotting element to grasp the suture material and form a knot for the stitch segment, and of forming a plurality of suture stitches in tissue including the steps of providing a length of suture material having a plurality of knotting elements spaced therealong to define stitch segments between a distalmost knotting element and an end of the suture material and a needle receiving the suture material, penetrating the tissue with the needle by moving the needle forwardly from an entry point to an exit point to allow positioning of a portion of the suture material at the exit point, grasping the suture material adjacent the exit point, withdrawing the needle from the tissue by moving the needle rearwardly and out of the entry point, engaging the grasped portion of the suture material with the distalmost knotting element to knot the stitch segment between the end of the suture material and the distalmost knotting element to form a first stitch, cutting the suture material proximally of the distalmost knotting element to define a new end for the suture material and a new distalmost knotting element and forming one or more additional stitches in tissue by repeating the penetrating, grasping withdrawing, engaging and cutting steps.

The knotting elements according to the present invention include an attachment site for slidably or fixedly receiving a first segment of a length of suture material and a grasping site for non-releasably engaging a second segment of the suture material to form a suture stitch with the knotting element effecting a knot for the suture stitch. The knotting elements can include various locking and/or gripping structure to enhance engagement of the suture material; and, subsequent to engagement of the suture material by the knotting element, the knotting element can be plastically deformed to further maintain the thusly formed suture stitch.

Other objects and advantages of the present invention will become apparent from the following description of the preferred embodiments taken in conjunction with the accompanying drawings.

BRIEF DESCRIPTION OF THE DRAWINGS

FIG. 1 is a broken perspective view, partly in section, of a suture supply according to the present invention.

FIGS. 4, 5, 6 and 7 are broken side views, partly in section, showing use of the suturing apparatus of the present invention.

FIG. 8 is a broken perspective view of a modification of a knotting element in accordance with the present invention.

FIG. 9 is a broken perspective view of another modification of a knotting element in accordance with the present invention.

FIG. 10 is a broken perspective view of an additional modification of a knotting element in accordance with the present invention.

FIG. 11 is a broken perspective view of a further modification of a knotting element in accordance with the present invention.

FIG. 12 is a broken side view of yet another modification of a knotting element in accordance with the present invention.

FIG. 13 is a broken side view of a further modification of a knotting element in accordance with the present invention.

FIG. 17 is a broken side view of a modification of a suturing apparatus according to the present invention.

FIGS. 18, 19, 20, 21 and 22 are broken side views, partly in section, showing use of the suturing apparatus of FIG. 17.

FIG. 23 is a broken perspective view illustrating another suturing procedure utilizing the suturing apparatus of FIG. 17.

FIG. 24 is a broken side view of a further modification of a suturing apparatus according to the present invention.

FIGS. 25, 26 and 27 are broken side views, partly in section, illustrating use of the suturing apparatus of FIG. 24.

FIG. 28 is a broken perspective view of another modification of a suturing apparatus according to the present invention.

FIG. 29 is a cross-sectional view of the suturing apparatus of FIG. 28.

FIGS. 30 and 31 are broken side views, partly in section, illustrating use of the suturing apparatus of FIGS. 28 and 29.

FIG. 33 is an exploded, broken side view, in section, of the suturing instrument of FIG. 32.

FIG. 37 is a broken perspective view of a suture supply according to the present invention.

FIG. 38 is a broken perspective view, partly in section, of another suture supply according to the present invention.

FIGS. 39 and 40 are broken side views, partly in section, of the suture supplies of FIGS. 37 and 38, respectively, forming suture apparatuses in combination with hollow needles.

FIG. 41 is a perspective view of another knotting element in accordance with the present invention.

FIG. 43 is a broken perspective view of a length of hollow suture material in accordance with the present invention.

FIG. 49 is a side view, partly in section, of a suture supply cartridge for use with the suturing instrument of FIG. 48.

FIG. 50 is a broken side view, partly in section, of the distal end of the suturing apparatus of FIG. 48 modified to include a needle.

FIG. 51 is a broken perspective view of the modified instrument of FIG. 50.

FIG. 52 is a side view, partly in section, of a single stitch suturing instrument according to the present invention.

DESCRIPTION OF THE PREFERRED EMBODIMENTS

Figure 2:
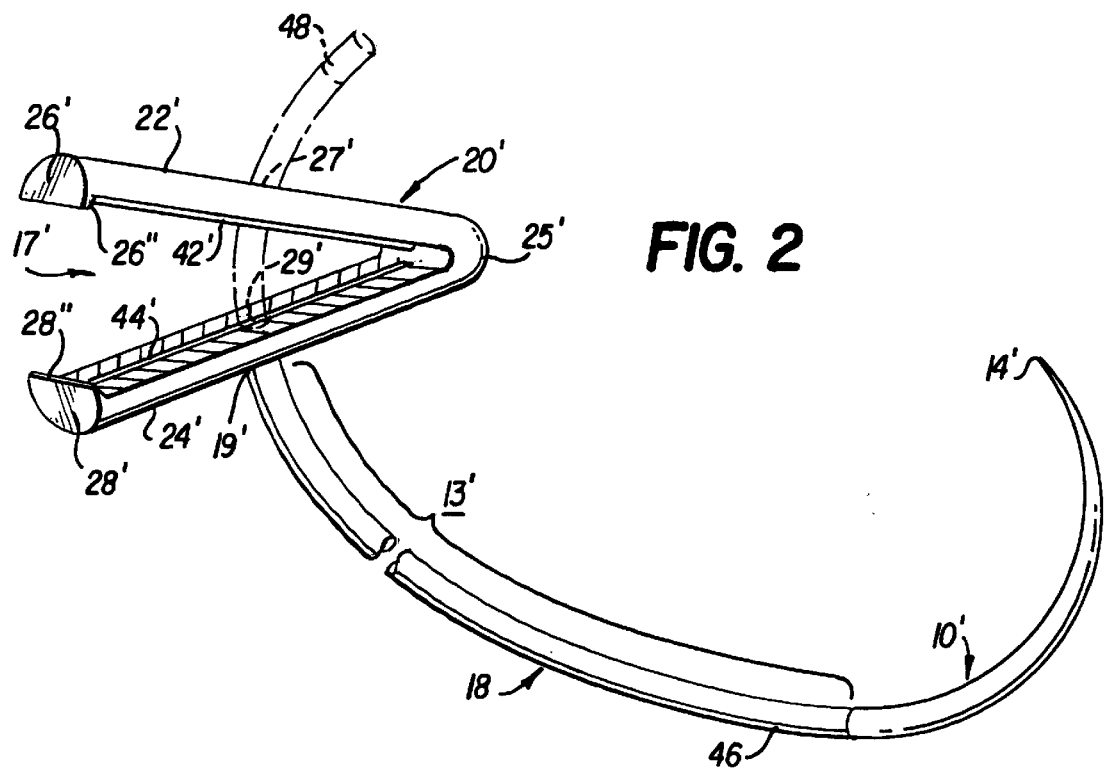
FIG. 2 is a broken perspective view of a suturing apparatus according to the present invention.

As used herein, the term "suturing" and forms thereof means passing a length of suture material through anatomical tissue, e.g. with the use of a needle or other penetrating member for approximation or holding of the tissue, or passing a length of suture material around anatomical tissue, e.g. for grasping the tissue or for constricting the tissue in the manner of ligation. Similarly, the term "stitch" and forms thereof as used herein means the formation of a loop of a length of suture material passing through anatomical tissue and/or around anatomical tissue by engagement of spaced segments of the suture material, e.g. forming a knot or otherwise joining the segments.

A suture supply in accordance with the present invention is shown in FIG. 1 and includes a length of filamentous suture material 18 carrying at least one knotting element 20, a plurality of knotting elements 20 being shown. The suture material 18 can be of any conventional filamentous construction, such as a monofilament or multifilament strand. The suture material can have a length dependent upon the type of stitch to be performed when a single knotting element is carried by the suture material; and, when a plurality of knotting elements are carried by the suture material, the length of the suture material can correspond to the number of stitches expected to be made or can be essentially indefinite by utilizing a package, such as a spool. The suture material can be solid or hollow; and, when the suture material is hollow, small holes can be formed in the wall of the suture material to communicate with the hollow interior thereof and various substances, such as medicaments, can be supplied within the hollow interior of the suture material to leach out through the holes and enter tissue in which the suture material is placed. The suture material can be made of non-stretchable or stretchable, absorbable or non-absorbable materials, and the suture material can have various outer diameter or cross-sectional sizes in accordance with procedural use including sizes suitable for use in microsurgical procedures, it being noted that the use of a stretchable suture material in accordance with the present invention is particularly advantageous in microsurgical procedures and other procedures, such as anastomosis, where space is limited.

Knotting elements 20 can be immovably secured to suture material 18 at predetermined spaced positions to define stitch segments therebetween or can be slidably carried by the suture material. Knotting elements according to the present invention have attachment sites for receiving a segment of the suture material prior to suturing and grasping sites for engaging another segment of the suture material after suturing to form a stitch. The attachment site of a knotting element according to the present invention is a location at which the knotting element is carried by the suture material either by immovable fixation or by sliding engagement, and the grasping site of a knotting element according to the present invention is a location at which the knotting element non-releasably engages the suture material to form a stitch such that a knotting element has the effect of tying a knot in a length of suture material.

The knotting elements 20 shown in FIG. 1 are each formed of a substantially spherical body 22 formed of a medical grade, absorbable or non-absorbable, plastically deformable material, integrally and unitarily defining an attachment site 24 and a grasping site 26. The attachment site 24 includes a bore or passage 28 passing through the body 22 and communicating with a space between a pair of opposed surfaces 30 and 32 forming the grasping site 26. The suture material 18 passes through the bore 28 such that the knotting element is carried by the suture material; and, when the knotting element is to be fixed to the suture material prior to suturing, the suture material can be bonded or mechanically clamped within the bore. When the knotting element is to be slidable relative to the suture material, after or just prior to suturing, the knotting element can be attached to the suture material via knurled protrusions on opposed surfaces 30 and 32 and/or via a transversely extending tongue or protrusion 34 on surface 30 movable to be received in an aligned transversely extending groove or recess 36 in surface 32 and/or providing the bore-suture material interface with a close tolerance or an irregular surface to hold the knotting element in place by friction which can be increased by providing the bore with a non-linear configuration, such as curved or serpentine. The body 22 is formed to define angularly oriented legs or jaws 38 and 40 carrying opposed surfaces 30 and 32, respectively, and a longitudinal tongue or protrusion 42 is disposed on surface 30 to be received in aligned longitudinal groove or recess 44. Accordingly, when the knotting elements are slidable along the suture material, the knotting elements can be held in place by friction or the jaws of the knotting elements can be partially closed to cause tongues 34 to be received in grooves 36 to fix the knotting elements at desired positions while the spaces or mouths formed by the opposed surfaces 30 and 32 remain open to receive another segment of the suture material prior to plastically deforming the jaws to grasp the suture material segment to form knot for a stitch.

The suture material 18 has a distal end 46 which can be received by a needle and a proximal end 48 which can be coated to form a rigid tail to aid manipulation of the adjacent knotting element 20.

The knotting elements can be formed of any suitable medical grade materials including metals, plastics and rubbers as well as bioabsorbable or non-bioabsorbable materials and can have various configurations and structure allowing the knotting elements to engage the segments of the suture material and to be plastically deformed to grip the suture material and/or to be locked in a position non-releasably grasping a suture material segment.

Suture apparatus according to the present invention is shown in FIG. 2 utilizing a length of filamentous suture material 18 and a knotting element 20' in the nature of a clip formed of a bent, V-shaped member of any suitable, medical grade material to have a pair of angled legs, jaws or opposing portions 22' and 24' terminating at distal ends 26' and 28', respectively. Legs 22' and 24' are joined to one another to converge at a junction or apex 25', and an attachment site 19' is disposed on leg 24' at which the knotting element is secured to a suture stitch segment 13' defined between the knotting element 20' and the distal end 46 of the suture material which is secured to the proximal end of a needle 10' having a sharp distal tip 14' for penetrating anatomical tissue. The knotting elements can have holes 27' and 29', respectively, in legs 22' and 24' thereof, as shown in phantom, through which the suture material extends to allow passage of the suture material entirely through the knotting element with the holes defining attachment sites 19'. The holes can be sized to secure the knotting element in a fixed position along suture material 18 or to permit the knotting element to be moved along the suture material to adjust the size of stitch segments. For example, the holes can be sized to frictionally retain the knotting element along the suture material while permitting the knotting element to be moved manually along the suture material with a force sufficient to overcome the frictional force. The holes can be arranged to be offset or not-aligned with one another when the knotting element is moved to a closed position to fix the position of the knotting elements along the suture material. Accordingly, once the knotting element is closed, the suture material passing through the knotting elements at attachment sites 19' will be gripped by the knotting element such that the knotting element will be in a fixed position along the suture material. The suture material 18 is shown in FIG. 2 as passing through holes 27' and 29' to form a tail 48 to manipulate the knotting element; however, the tail 48 can be secured to leg 22' without a portion of the suture material extending between legs 22' and 24' or can be secured at any position on the knotting element.

The knotting element 20' is normally disposed in an open or suture material-receiving position wherein the distal ends 26' and 28' of legs 22' and 24', respectively, are spaced from one another at an angle to define an opening or mouth 17' therebetween, and the inner opposed surfaces of legs 22' and 24' define a grasping site for engaging the second segments of suture material as explained further below. The opposed surfaces of the legs 22' and 24' are preferably irregular and provided with gripping structure such as knurling, serrations, teeth, barbs, pins, ridges, ribs or the like for gripping the suture material and/or for being disposed in mating engagement with corresponding or complementary structure on the surfaces of opposing legs when the knotting element is moved to a closed or suture material grasping position. For example, the inner surface of leg 24' can be provided with a longitudinal groove 44' within which the suture material can be compressed or trapped when the clip is moved to the closed position, and the inner surface opposed to groove 44' can have a longitudinal protrusion or tongue thereon, such as tongue 42', for mating with groove 44'. It is preferred that the gripping structure be oriented in a direction transverse to the direction in which the second segment of suture material extends to resist disengagement of the suture material from the knotting element. The knotting elements can include various locking structure for securing the knotting elements in the closed position. The locking structure can be formed by the gripping structure or separately therefrom. For example, the end 26' of leg 22' can be configured to define an inwardly extending finger or flange 26" to be disposed in overlapping arrangement with an outwardly extending finger or flange 28" on the distal end 28' of leg 24' with a snap fit in the closed position to provide locking structure at the distal ends. The knotting elements can be secured to the suture material in various manners to be in a fixed position along the length of suture material or to be movable along the length of suture material, including mechanically, being formed integrally, unitarily with the suture material, fusing, welding, molding and the like. The manner in which the knotting elements are secured to the suture material as well as the location of the attachment sites can be selected to permit the knotting elements to be optimally oriented during use in accordance with the suturing procedure to be performed. For example, although the suture material 18 extends through legs 22' and 24' transverse to the length of the legs, the suture material can also extend lengthwise through a bore or passage in one or both of the legs or lengthwise between the legs via a hole at the apex 25'. Although the suture material is described as being a continuous length in FIGS. 1 and 2 extending entirely through the knotting elements, the suture material can be discontinuous to terminate at the attachment sites on each knotting element without extending through any of the knotting elements. The knotting elements can be moved to the closed position and plastically deformed with the use of conventional instruments including graspers, clamps, forceps or the like.

Figure 3:
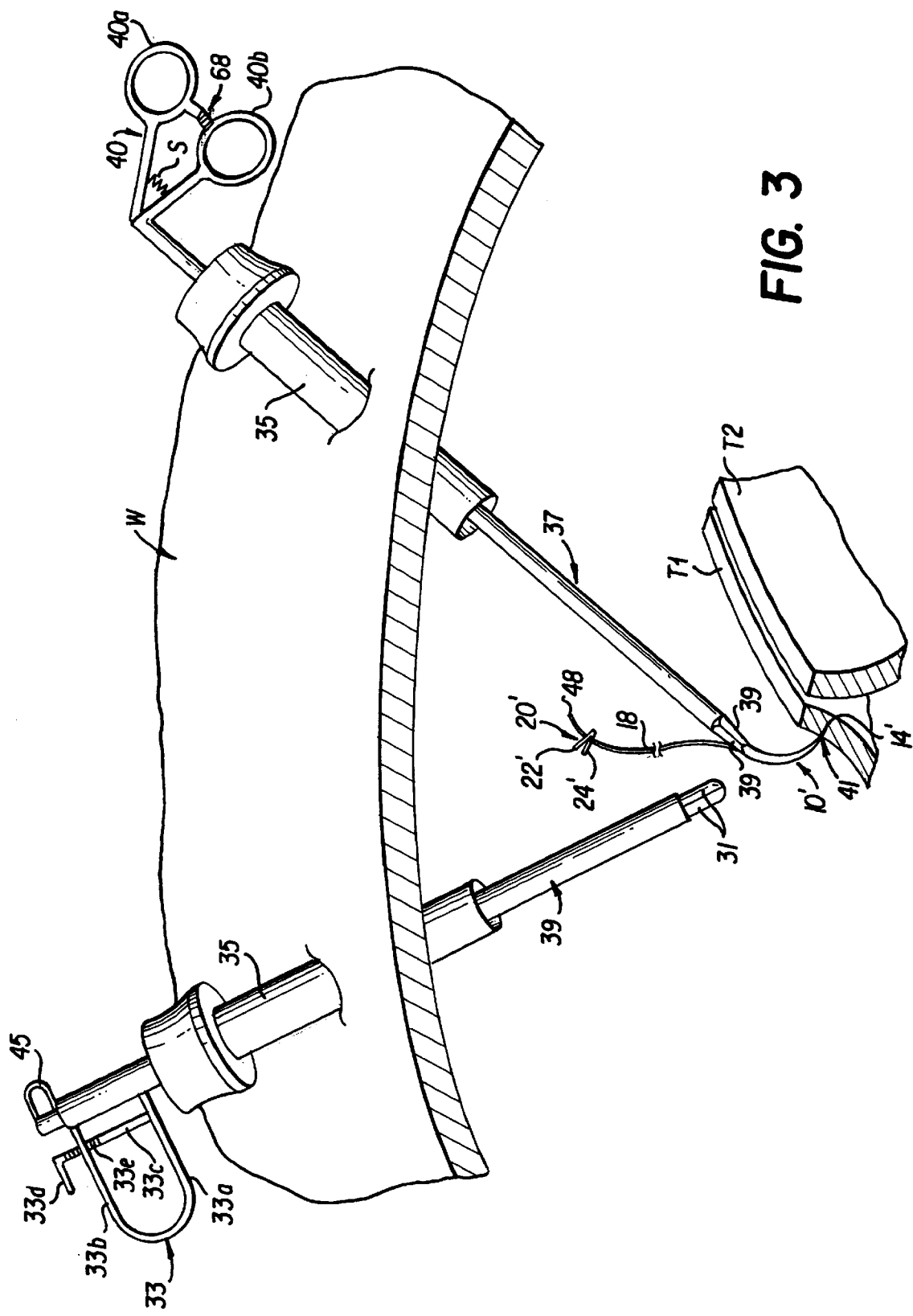
FIG. 3 is a broken perspective view, partly in section, illustrating suturing according to the present invention during an endoscopic procedure.

FIG. 3 illustrates use of the suturing apparatus of FIG. 2 during an endoscopic procedure wherein portal sleeves 31 and 35 are introduced through an anatomical cavity wall W with the use of penetrating members such as trocars, not shown. The suturing apparatus has a single knotting element 20' carried at a proximal end of the length of suture material 18. The distal end of the suture material is coupled with the needle 10' at the proximal end thereof; however, the position at which the suture material is coupled to the needle can be anywhere along the body of the needle. A needle holder 37 is introduced into the cavity through portal sleeve 35, and a grasping instrument 39 is introduced into the cavity through portal sleeve 35. The needle holder 37 includes movable jaws 39 at a distal end thereof for holding the proximal end of needle 10', the jaws being carried by an operating member having a length to extend through portal sleeve 35 to a proximal end coupled with a handle 40. The handle 40 is formed of a finger grip member 40a pivotally mounted on a finger grip member 40b via a pin and spring biased, as shown schematically at S, toward finger grip member 40b such that jaws 39 are normally closed and are movable to an open position by moving finger grip member 40a away from finger grip member 40b against the bias of spring S. Once a needle is placed within the jaws, releasing the finger grip members will allow the jaws to continuously grip the needle with the spring force. If it is desired to hold the needle with a greater force, the finger grip members are squeezed, and a ratchet mechanism 68 holds the jaws in the increased force position. Of course, conventional needle holders, sometimes also referred to as needle drivers or needle graspers, for use in endoscopic surgery can be used with the suturing apparatus of the present invention.

To suture tissue portions T1 and T2, needle holder 37 is manipulated to drive needle tip 14' distally or forwardly through an entry point 41 in tissue portion T1 and then through tissue portion T2 and out of tissue portion T2 at an exit point 43 carrying the suture material 18 through the tissue portions as shown in FIG. 4. Once needle 10' has passed through tissue portion T2, the segment 49 of suture material extending from exit point 43 is pulled distally until the knotting element 20' contacts tissue portion T1 at the entry point 41. Segment 49 is then drawn back over the tissue portions T1 and T2 to the entry point 41. The segment 49 is positioned to be engaged by the knotting element 20' to be received between legs 22' and 24' such that a stitch is formed extending from the knotting element through the tissue and back to the knotting element with the knotting element effecting or serving as a knot for the suture stitch.

Grasping instrument 39 can be used to grasp knotting element 20' while the suture material segment 49 is placed at the grasping site of the knotting element and includes a pair of normally closed opposed jaws 31 at a distal end thereof having inner configurations to facilitate grasping of knotting elements and of tail 48 such as knurled or serrated surfaces and/or recesses conforming to the shape of a knotting element to be grasped and closed. The grasping instrument 39 has a length to extend from the distal end at the surgical field within the anatomical cavity through the portal sleeve 35 to a proximal end external of the anatomical cavity. A U-shaped spring handle 33 at the proximal end of the grasping instrument has opposing legs 33a and 33b having a normal position spring biasing the jaws 31 to the closed position. An arm or cross bar 33c extends proximally from leg 33a to terminate at a trigger 33d and carries ratchet teeth 33e for engaging teeth carried by leg 33b. While jaws 31 are shown as being movable angularly away from the longitudinal axis of the instrument, the jaws can be arranged transversely such that one jaw is stationary and the other jaw moves longitudinally in an up/down fashion looking at FIG. 3. A U-shaped handle 45 is also shown at the proximal end of the grasping instrument and can be used to eject knotting elements according to the present invention as will be explained hereinafter. To open jaws 31, handle legs 33a and 33b are squeezed together; and, once the jaws are positioned adjacent the knotting element 20' or the tail 48, the jaws will close by spring power to grasp the knotting element or the tail to assist in orienting the mouth of the knotting element to receive the suture material segment 49.

Once the knotting element 20' has been drawn up against the tissue and segment 49 has been brought back over the tissue to be received by knotting element 20', tension is applied to the suture material to tighten the suture stitch to adjustably approximate tissue portions T1 and T2 as shown in FIG. 6. Thereafter, knotting element 20' is moved to the closed position and is plastically deformed utilizing grasping instrument 39 by squeezing leg 33b and trigger 33d to clamp legs 22' and 24' together to grip the suture material and secure the thusly formed tensioned suture to complete the stitch as shown in FIG. 7. The suture material is then cut, and the needle is removed from the body. Although the suturing procedure has been described for two tissue portions T1 and T2, it should be appreciated that the procedure is applicable to suturing of various tissue structures including single and multiple tissue structures, puncture site and wound closures and ligation, for example.

FIGS. 8–15 illustrate various, exemplary alternative knotting elements according to the present invention. FIG. 8 illustrates a knotting element 120 secured to a length of suture material 118 and having a spherical configuration with a wedge or V-shaped notch or opening 117 defined between opposing portions 122 and 124 of knotting element 120 in an open position with the opposed inner surfaces of portions 122 and 124 defining a grasping site. Knotting element 120 is deformable to move opposing portions 122 and 124 toward one another to reduce the size of or to close the opening 117 to grip a segment of suture material 118 in a closed position. Locking structure for knotting element 120 includes a pin 121 protruding from an inner surface of knotting element portion 122 at a distal end thereof and an aperture 123 in the inner surface of knotting element portion 124 to receive pin 121 in the closed position. Additionally, the inner opposed surfaces of opposing portions 122 and 124 are serrated to grip the suture material, and the serrations extend in a direction transverse to the direction in which the suture material segment extends when engaged by the opposed inner surfaces. Suture material 118 is secured to knotting element 120 at an attachment site 119 aligned with the knotting element opening at the convergence of portions 122 and 124; however, attachment site 119 can be disposed at various other locations along knotting element 120 not aligned with the opening, and the suture material can terminate at the knotting element or extend entirely through the knotting element.

FIG. 9 illustrates a knotting element 220 having a configuration similar to that of a conventional ligating clip. Knotting element 220 includes a pair of proximal or base legs 222 and 224 angularly joined to one another to converge at an apex at attachment site 219 for suture material 218 and a pair of opposing distal legs 222' and 224' extending distally from base legs 222 and 224, respectively. The inner surface of legs 224 and 224' are knurled and provided with a groove 225 for receiving a tongue 226 carried by legs 222 and 222'. Knotting element 220 is normally disposed in an open position with distal legs 222' and 224' spaced from and parallel with one another to define an opening 217 therebetween. Knotting element 220 is plastically deformable to move distal legs 222' and 224' toward one another causing the serrated inner surfaces thereof to grip a segment of suture material 218 in a closed position. Although attachment site 219 is illustrated as being aligned with the apex of proximal legs 222 and 224, the attachment site 219 can be disposed at various other locations along knotting element 220 including along or through either of distal legs 222' and 224', and the suture material can terminate at the knotting element or extend entirely through the knotting element.

The knotting element 320 illustrated in FIG. 10 includes opposing portions formed as a pair of planar, circular disks 322 and 324 separated from one another by a cylindrical spacer 325 to be normally disposed in spaced, parallel relationship in an open position wherein an opening or space 317 is defined between inner opposed surfaces of the disks for receiving a segment of suture material 318. Suture material 318 is secured to disk 322 at an attachment site 319 at a mid-point thereof; however, the suture material 318 can be secured to knotting element 320 at various other locations and can terminate at the knotting element or extend entirely through the knotting element. Knotting element 320 is deformable or compressible in the direction of the arrows A to move or compress disks 322 and 324 toward one another to grip a segment of suture material 318 in a closed position, the inner surfaces of disks 322 and 324 being knurled and carrying radial extending tongue and groove arrangements. With the use of knotting element 320, the suture material 318 can be wrapped or wound around spacer 325, which has an outer diameter less than the outer diameter of disks 322 and 324, prior to movement of the knotting element to the closed position for enhanced securement. Spacer 325 can be constructed in many various ways to permit disks 322 and 324 to be moved toward one another including as a telescoping member or as a member movable into either or both of the disks in the closed position. Although the suture material is shown as being arranged centrally with disk 322, the suture material can be arranged offset or non-centrally with the knotting element. Various locking structures can be provided in knotting element 320 to provide a one-way action allowing movement of the disks toward the closed position and preventing movement of the disks toward the open position, such locking structures including ratchet teeth and other one-way mechanisms. The opposing portions do not have to be planar or disk-like, and the knotting element 320 can be arranged transversely such that one of the opposing portions is alongside the suture material.

Knotting element 420 illustrated in FIG. 11 is configured as a cube or block having a V-shaped or wedge-shaped cut-out or notch therein defining an opening 417 for receiving a segment of suture material 418 between opposed inner surfaces of opposing portions 422 and 424. Knotting element 420 is normally disposed in an open position with portions 422 and 424 spaced from one another to define the opening and is movable to a closed position to move the portions 422 and 424 toward one another to close or reduce the size of the opening 417. An inner surface of knotting element portion 424 has a raised, longitudinal ridge or tongue 421 thereon for being received in a corresponding slot or groove in an inner surface of knotting element portion 422 when the knotting element is moved to the closed position and plastically deformed. Knotting element 420 can have one or more lengths of suture material secured thereto and is shown with three lengths of suture material 418, 418' and 418" secured at different attachment sites 419, 419' and 419" allowing a selected one or more of the lengths of suture material to be used to suture tissue; however, one or more of the lengths of suture material can pass entirely through the knotting element.

Knotting element 520 illustrated in FIG. 12 is similar to knotting element 20' except that leg 522 has an inwardly protruding distal flange 526 terminating at an angled surface forming a lip 543 protruding in the direction of the apex of legs 522 and 524, which is also the attachment site 519. Leg 524 terminates at an angled distal end 528 normally disposed adjacent angled surface 527 in an open position for knotting element 520 wherein an opening 517 for receiving a segment of suture material is circumscribed by legs 522 and 524 and by flange 526. Legs 522 and 524 are preferably knurled and provided with longitudinal tongue and groove arrangements. Knotting element 520 is movable to a closed position wherein legs 522 and 524 are brought toward one another with the angled distal end 528 of leg 524 cooperating with angled surface 527 to permit leg 524 to be moved inwardly of lip 543 to be held thereby with a snap fit when the knotting element is deformed. A length of suture material 518 is secured at attachment site 519' at the apex of legs 522 and 524; however, the suture material can pass entirely through the knotting element.

Knotting element 620 illustrated in FIG. 13 is representative of a spring-loaded knotting element according to the present invention and includes a generally U-shaped member having opposing legs 622 and 624 extending distally from a curved base 644. One of the legs, leg 622, has a hole therein through which suture material 618 passes to form an attachment site 619 securing the knotting element to the suture material. Attachment site 619 is close to the apex or junction for legs 622 and 624; however, the attachment site can be anywhere along leg 622. Suture material 618 passes through leg 622 transverse or perpendicular to the length of leg 622; however, the suture material can extend lengthwise through a hole in leg 622 in which case the knotting element will be oriented 90° from the position shown in FIG. 13. Legs 622 and 624 are spring-biased to be normally disposed in an initial closed position wherein inner opposed surfaces of the legs are disposed closely adjacent one another such that no opening is defined between the legs or only a minimal opening 617 is defined therebetween. Legs 622 and 624 can be biased to the initial closed position in various ways including forming the knotting element of spring material or components. Legs 622 and 624 have tapered distal ends 626 and 628 defining a flared or enlarged smooth entry or guide area leading into opening 617, and legs 622 and 624 are preferably knurled and provided with longitudinal tongue and groove arrangements as shown at 627. In use, knotting element 620 can be manually moved to an open position with the use of a suitable instrument, such as forceps, to spread or move legs 622 and 624 away from one another to permit a segment of suture material 618 to be positioned between the legs as facilitated by the guide at the distal ends of the legs. Alternatively, the suture material can be forcibly inserted or slid between the legs 622 and 624. Once the suture material has been positioned as desired between legs 622 and 624 to form a suture stitch, the knotting element 620 can be plastically deformed to further compress legs 622 and 624 and move the knotting element to a second or final closed position to secure the suture stitch. With the use of spring-loaded knotting elements, deformation of the knotting elements to secure the suture stitch may not be required; however, deformation of the knotting element is desirable for added protection or securement.

Figure 14:
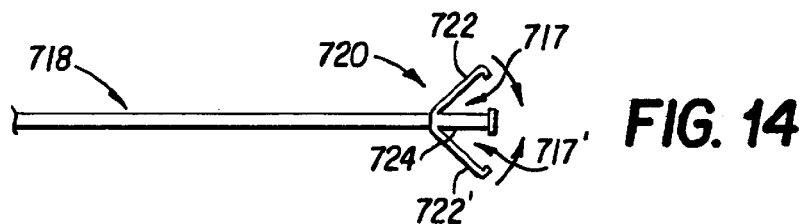
FIG. 14 is a broken side view of yet another modification of a knotting element in accordance with the present invention.

FIG. 14 illustrates a knotting element 720 that is similar to knotting element 20' except that knotting element 720 has two outer legs 722 and 722' cooperating with an inner leg 724 to define first and second grasping sites for engaging a segment of suture material 718. Knotting element 720 is normally disposed in an open position with a first opening 717 defined between legs 722 and 724 and a second opening 717' defined between legs 722' and 724 such that either or both of the first and second openings can receive a segment of suture material 718 during use. Knotting element 720 is movable to a closed position wherein legs 722 and 722' are brought toward one another and toward leg 724 to grip the segment of suture material. Although the suture material is shown as terminating at the knotting element, it should be appreciated that the suture material can pass through the knotting element with openings 117 and 117' disposed on opposite sides of the suture material such that the suture material extends between the openings or the openings can both be disposed on the same side of the suture material.

Figure 15:
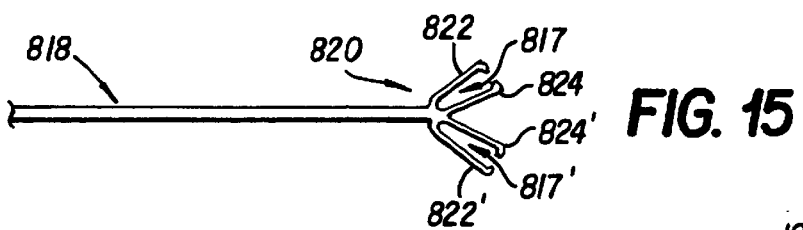
FIG. 15 is a broken side view of still another modification of a knotting element in accordance with the present invention.

An additional knotting element 820 is illustrated in FIG. 15 and is similar to knotting element 720 except that knotting element 820 includes two outer legs 822 and 822' and two inner legs 824 and 824'. Inner legs 824 and 824' are disposed at an angle with one another to define a gap or space therebetween. In the open position, legs 822 and 824 are spaced from one another to define a first opening 817 therebetween, and legs 822' and 824' are spaced from one another to define a second opening 817' therebetween. Accordingly, a segment of suture material 818 can be positioned within either or both of the first and second openings; and, thereafter, the knotting element 820 is movable to compress the legs toward one another.

Figure 16A:
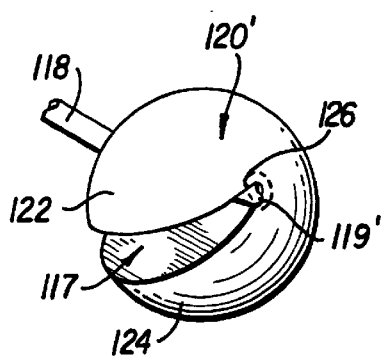
FIG. 16A is a broken perspective view illustrating one manner of securing a knotting element to a length of suture material according to the present invention.

FIG. 16A illustrates a knotting element 120' similar to knotting element 120 of FIG. 8 defining opening 117 between opposing portions or jaws 122 and 124. The opening 117 terminates within the knotting element 120' at a transverse channel or passage 126 within which suture material 118 extends to define an attachment site 119' for the suture material. Knotting element 120' is partially compressed or deformed to reduce the cross-sectional size of channel 126 to non-releasably secure the suture material 118 therein at attachment site 119'. With the suture material non-releasably secured in channel 126, the knotting element 120' remains in an open position as shown such that the suture material 118 can be placed in opening 117 between the inner surfaces of opposing portions 122 and 124 for use as described above. The knotting element 120' can be movable along the length of suture material or the position of the knotting element along the length of suture material can be fixed. For example, the knotting element 120' can be initially plastically deformed to close channel 126 an amount sufficient to fix the position of the knotting element along the suture material, or the knotting element 120' can be compressed an amount sufficient to prevent withdrawal of knotting element 120' from the length of suture material 118 in a direction transverse to the length of suture material while permitting the knotting element 120' to be moved longitudinally along the length of suture material for adjustment during use.

Figure 16B:
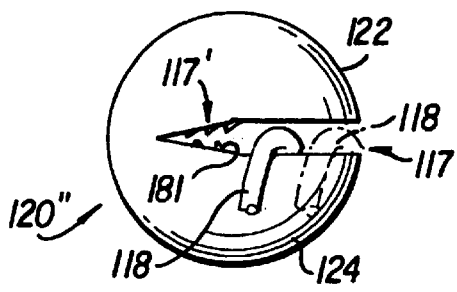
FIG. 16B is a side view of a modified knotting element in accordance with the present invention illustrating another manner of securing the knotting element to a length of suture material.
Figure 16C:
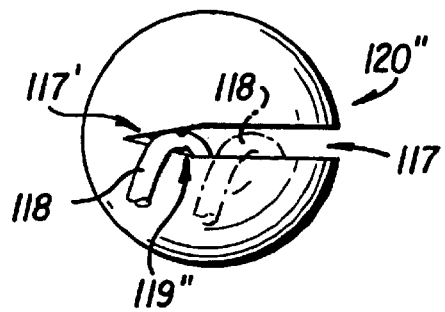
FIG. 16C is a broken side view showing the knotting element of FIG. 16B secured to the length of suture material.
Figure 16D:
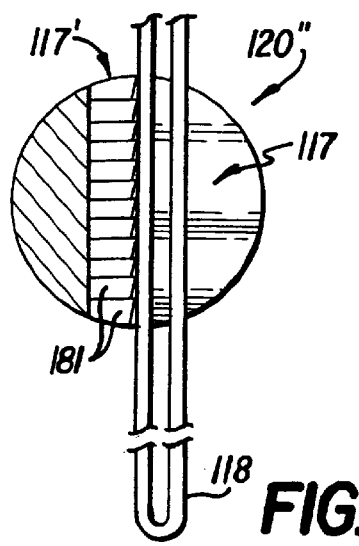
FIG. 16D is a sectional view of the knotting element of FIG. 16B.

Another manner in which a knotting element can be secured to a length of suture material 118 is illustrated in FIGS. 16B and 16C. As shown in FIG. 16B, knotting element 120" has a cut-out or slot therein defining opening 117 between inner, parallel opposed surfaces of opposing portions 122 and 124. The opening 117 terminates within knotting element 120" at a second, tapered slot or opening 117" defined between inner, angled opposed surfaces of opposing portions 122 and 124. A plurality of teeth or barbs 181 are disposed along the opposing angled surfaces for gripping a segment of suture material 118 positioned transversely within the opening 117' as shown in FIG. 16C. The opening 117 has a height between the parallel surfaces that preferably is equal to or slightly less than the outer diameter or cross-sectional size of suture material 118, and the opening 117' has a configuration and size to cause gripping of the suture material by barbs 181 and/or the angled surfaces. Accordingly, a segment of suture material 118 can be inserted in the opening 117 for frictional retention therein allowing the knotting element to be movable along the suture material as shown in FIG. 16B. When it is desired to fix the position of the knotting element along the suture material, the suture material segment is moved into opening 117' to be held in place at attachment site 119" by barbs 181 and/or the angled opposed surfaces as shown in FIG. 16C. Although the holding force of barbs 181 and/or the angled surfaces may be sufficient to secure the suture material, the knotting element can be deformed for additional protection and securement. The knotting element 120" is particularly useful in securing a loop formed by the suture material to be placed around tissue to be ligated to produce a free tie in that both ends of the loop can be positioned in opening 117 as shown in phantom in FIGS. 16B and 16C and in FIG. 16D at which time the knotting element can be pushed distally to close the loop around the tissue. Once the loop is tightened to the desired tension, both ends of the loop can be positioned in opening 117" to secure the tightened loop in place around the tissue or the opposed portions can be plastically deformed to tie the stitch.

Figure 16E:
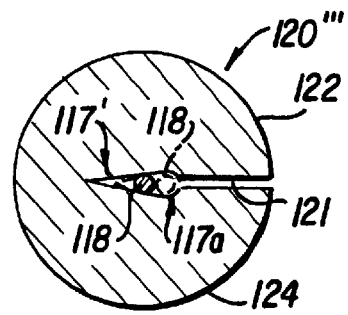
FIG. 16E is a cross section of a modification of the knotting element of FIG. 16B.

A knotting element 120''', which is a variation of knotting element 120", is shown in FIG. 16E in cross section with the primary change being that an opening 117a is formed in the center of the knotting element and the knotting element is made of a resilient material to permit opposing portions 122 and 124 to be spread apart to permit suture material segments 118 to enter opening 117a through a space 121 such that the suture material segments are captured within the knotting element during sliding movement of the knotting element therealong.

A modified suturing apparatus according to the present invention is illustrated in FIG. 17 and includes a suture needle 810 having a straight configuration and terminating distally at a sharp distal end 814 which is also an attachment position 811 for a distal end of a length of suture material 818. A knotting element 820, shown schematically, is secured to a proximal end of the suture material 818 at attachment site 819 with the suture material 818 terminating at the knotting element or extending through the knotting element to form a tail as shown in phantom.

FIGS. 18–21 illustrate use of the suturing apparatus of FIG. 17 to suture tissue portions T1 and T2. The sharp distal end 814 of needle 810 is driven distally through entry point 841 to pass through tissue portions T1 and T2 to exit tissue portion T2 at exit point 843 such that the suture material 818 passes through both tissue portions and exits tissue portion T2 along with the needle. When tip 814 and attachment position 811 have passed through tissue portion T2, a portion of the suture material is exposed and will bulge outwardly away from the needle to form a loop segment 846 spaced from the needle body when the needle is backed out or moved proximally slightly. An instrument 830 having a curved jaw 831 is moved to insert the jaw 831 in the loop segment 846 as shown in FIG. 19, and the loop segment 846 is manipulated with instrument 830 to be brought back over tissue portion T2 and placed within the knotting element 820 which is pulled tight against the tissue T1 at the entry point or is drawn over tissue portion T1 as shown in FIG. 20. The segment 851 of suture material 818 extending from tissue portion T1 is grasped and pulled to apply tension to the suture material and adjustably approximate tissue portions T1 and T2 as shown in FIG. 21. Once the tissue portions T1 and T2 have been approximated as desired, the segment 851 is positioned within the knotting element 820, and the knotting element 820 is closed and deformed to secure the thusly formed tensioned stitch. The needle is then severed from the suture material and removed from the body.

An alternative step in use of the suturing apparatus of FIG. 17 is illustrated in FIG. 22 wherein the loop segment 846 is placed behind or around the knotting element 820 prior to tensioning with segment 851.

FIG. 23 illustrates another alternative step in use of the suturing apparatus of FIG. 17 wherein the loop segment 846 is placed within the opening of knotting element 820 to protrude from a side of the knotting element. The segment 851 is then passed through the loop 846 and pulled to approximate the tissue portions T1 and T2. Various other tying techniques can be accomplished with the suturing apparatus of FIG. 17 dependent upon the tissue being sutured, the nature of the suture material and the configuration of the knotting element.

A modification of a suturing apparatus according to the present invention is illustrated in FIG. 24 and includes a suture needle 910, a length of suture material 918 and a knotting element shown schematically at 920. Needle 910 is similar to needle 810 except that needle 910 has a sharp distal end 914 and a sharp proximal end 916 for penetrating anatomical tissue. Suture material 918 is attached to needle 910 at an attachment position 911 midway between the needle distal and proximal ends.

In use, the distal end 914 of needle 910 is driven distally through an entry point 941 to pass through tissue portions T1 and T2 to exit tissue portion T2 at an exit point 942 as shown in FIG. 25. Once the needle 910 has passed entirely through tissue portion T2, the proximal end 916 is driven proximally or rearwardly through an entry point 941' on tissue portion T2 spaced from exit point 942 as shown in FIG. 26. The needle is driven proximally through tissue portions T2 and T1 to exit tissue portion T1 at an exit point 942' spaced from entry point 941. The segment 951 of suture material 918 extending from the exit point 942' is grasped and positioned in the knotting element 920 and is pulled to adjustably approximate the tissue portions T1 and T2 subsequent to which the knotting element 920 is deformed to secure the thusly formed suture stitch. The needle is then cut from the suture material and removed from the body.

An additional modification of a suturing apparatus according to the present invention is illustrated in FIG. 28 and includes a hollow needle 1010 having a sharp, open distal end 1014, a length of suture material 1018 and a knotting element, schematically shown at 1020 to be similar to knotting element 620, having an attachment site 1019 along a leg 1024 securing the knotting element to a proximal end of suture material 1018. Use of the suturing apparatus of FIG. 28 is similar to that previously described in that the sharp distal end 1014 of needle 1010 is utilized to penetrate tissue to be sutured, and the length of suture material 1018 is utilized to form a suture with the knotting element 1020 securing a segment of the suture material. The knotting element 1020 does not have to be deformed in that the spring force of the knotting element ensures that the suture material is held firmly; however, it is preferred that the knotting element be deformed for redundant securement. As shown in FIG. 29 needle 1010 is hollow, and a slot 1047 is formed in the wall of the needle to communicate with the lumen thereof, the slot 1047 extending the entire length of the needle 1010. Slot 1047 preferably has a width just large enough in size to allow suture material 1018 to pass therethrough as explained further below; and, while the suture material is shown in FIG. 29 as having a diameter substantially less than the diameter of the needle lumen, the suture material can be of a size to fill any portion of the needle lumen with a corresponding size for slot 1047.

FIGS. 30 and 31 illustrate use of the suturing apparatus of FIG. 28 and FIG. 29. The distal end 1014 of needle 1010 is driven distally through an entry point 1041 and passed through tissue portions T1 and T2 to exit tissue portion T2 at an exit point 1042. Once the segment 1051 of the suture material has passed through tissue portion T2 as shown in FIG. 30, needle 1010 is moved proximally causing the suture material to pass through slot 1047 and withdrawn or backed out proximally from tissue portions T1 and T2 leaving the suture material in place. The segment 1051 is grasped, positioned in knotting element 1020 and pulled to tension the suture stitch and adjustably approximate tissue portions T1 and T2 with the knotting element 1020 disposed in contact with the tissue at entry point 1041. Thereafter, knotting element 1020 is deformed for additional securement of the thusly formed suture stitch, and the suture material is cut and the needle removed from the body.

Figure 32:
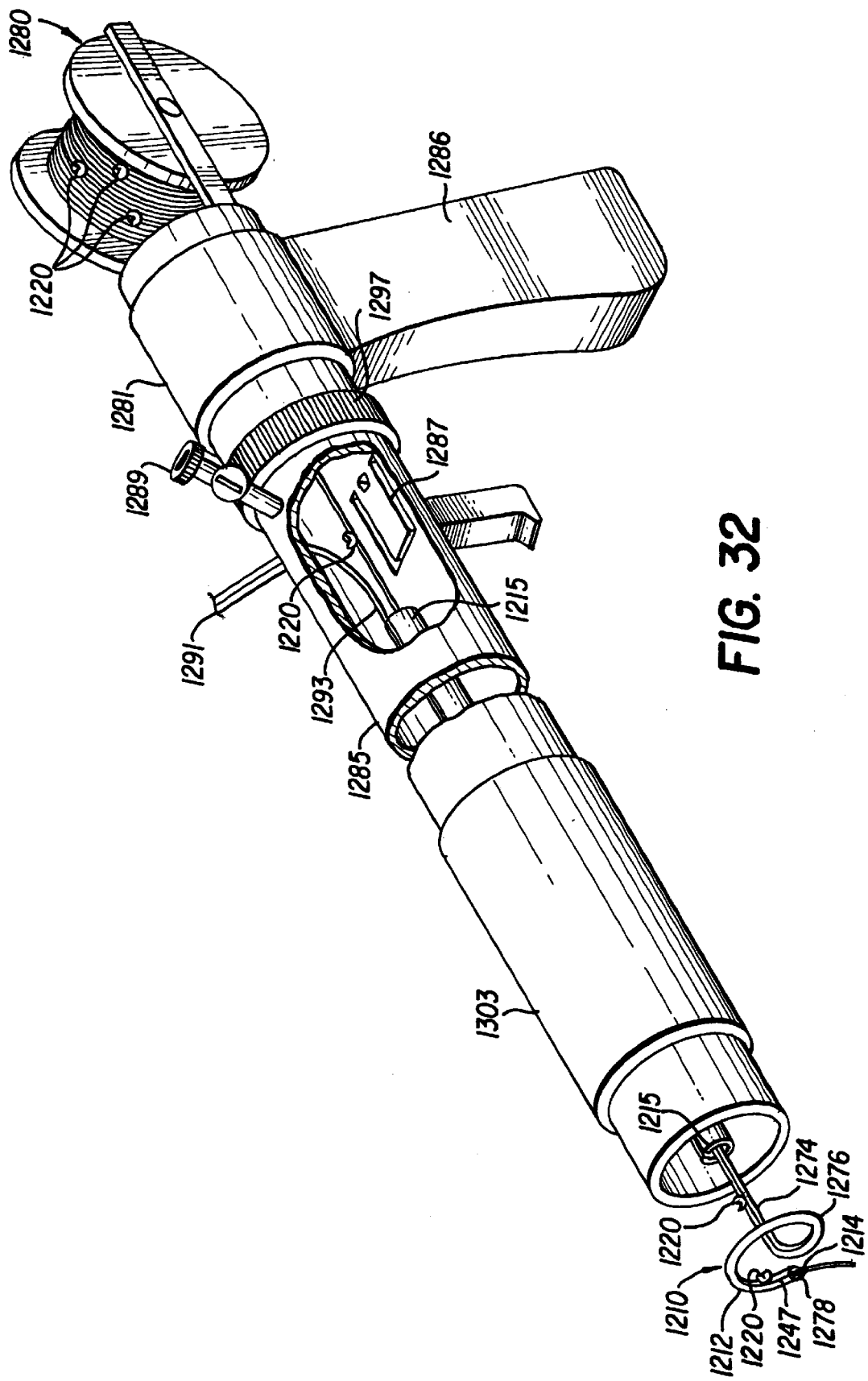
FIG. 32 is a broken side view of a suturing instrument in accordance with the present invention.

FIG. 32 illustrates a suturing instrument according to the present invention incorporating a hollow needle 1210 including a body 1212 having a substantially straight portion 1274 and an arcuate portion 1276 disposed at a distal end of the straight portion. Straight portion 1274 is coupled or formed integrally, unitarily with a hollow elongate tube 1215 having a proximal end disposed in spaced relation with a suture supply including a wheel or spool 1280 removably mounted on a proximal end of the instrument adjacent a handle 1286. Arcuate needle body portion 1276 terminates distally at a distal end 1214 having a sharp tip. Body 1212 is hollow to communicate with the lumen of elongate member 1215, and a slot 1247 is formed in needle body 1212 to communicate with the lumen therein in the manner shown in FIG. 29. The suture supply includes a length of suture material 1218 carrying a plurality of spaced knotting elements schematically shown at 1220 with the suture material extending between knotting elements corresponding to stitch segments. The suture supply, including the suture material and knotting elements wound on wheel 1280, is removably mounted within a collar 1281 secured to a handle 1286. Suture material 1218 and knotting elements 1220 pass through elongate member 1215, and suture material 1218 passes through needle 1210 with knotting elements 1220 disposed externally of the needle and connected to the suture material through slot 1247. A segment of the suture material extends from the distal end 1214 of the needle and can be secured in a notch 1278 in the needle distal end to pull the suture material with the needle as the needle penetrates tissue. Alternatively, the suture material can be driven or pushed through the needle by means of friction rollers, not shown, or by means of a control trigger 1283 pivotally mounted on an elongate tubular barrel 1285 to pivot a pusher 1287 such that pulling the trigger 1283 causes the pusher 1285 to engage a knotting element 1220 to advance the knotting element and the suture material through member 1215 and needle 1210.

One or more angled stop cocks 1289 can communicate with the interior of barrel 1285 to permit irrigation, aspiration and access for various flexible instruments, and an electrosurgical connector 1291 can be mounted on the barrel 1285 and connected with the needle 1210 via a wire 1293 to permit use of the needle for electrosurgical backup, such as for cauterization and/or cutting. Of course, surrounding components will be made of non-conducting materials when an electrosurgical connector is provided. As shown in FIG. 33, the barrel 1285 is mounted to be rotatable relative to the handle 1286 by mounting a flange 1295 on a proximal end of the barrel within collar 1281 so as to be rotatable therein via a knurled ring 1297. The suture supply 1280 has a coupling 1299 of a size to be frictionally received within a coupling 1301 rotatably received in collar 1281 to permit rotation of the suture supply with the barrel. Preferably, a slidable sheath 1303 is movable along the sleeve to cover and protect the needle.

Figure 34:
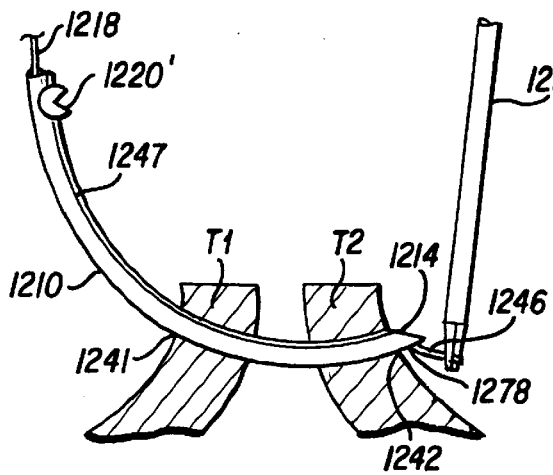
FIGS. 34, 35 and 36 are broken side views, partly in section, illustrating use of the suturing apparatus of FIG. 32.
Figure 35:
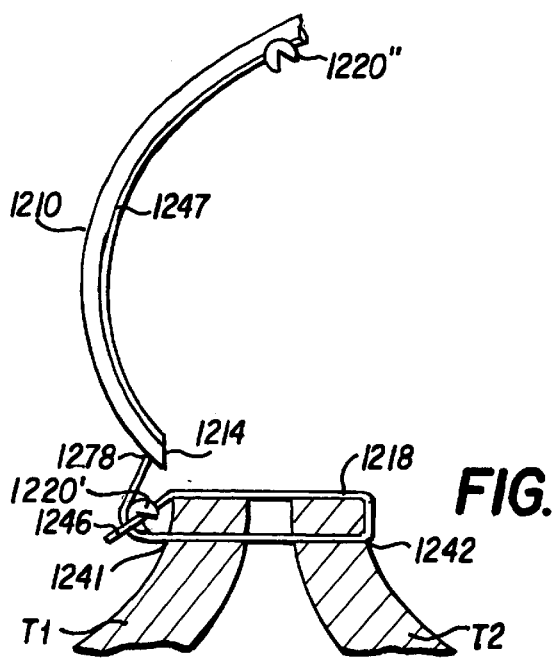

Use of the suturing instrument of FIG. 32 will be described with reference to FIGS. 34–36 with the needle 1210 driven forwardly or distally through tissue with a rotating or arcuate motion. Arcuate movement of the needle can be accomplished by turning barrel 1285 relative to handle 1286 or by turning the entire instrument during penetration. As noted above, suture material 1218 has a distal end 1246 which can be held in needle 1210, for example via notch 1278, to pull the suture material through tissue along with the needle or the suture material can be pushed or driven through the needle after tissue is penetrated, for example via operation of trigger 1283. As shown in FIG. 34, the tip 1214 of needle 1210 is driven through an entry point 1241 in tissue portion T1 and is passed through tissue portions T1 and T2 to exit tissue portion T2 at an exit point 1242. Once the distal end or segment 1246 of the suture material secured in notch 1278 has exited tissue portion T2, an instrument 1237 is utilized to grasp the distal end of the suture material adjacent the exit point. Instrument 1237 is manipulated to remove the suture material from the notch 1278, and the needle 1210 is moved proximally or backed out through tissue portions T1 and T2 along the length of the suture material to exit the tissue portions at the entry point while the suture material is held by instrument 1237. The needle is moved proximally along the suture material until the distal end 1214 of the needle is positioned just proximally of the distalmost knotting element, i.e. schematically shown knotting element 1220'. Instrument 1237 is then manipulated to pull the suture material through the tissue until knotting element 1220' is adjacent or contacts the tissue at the entry point. Segment 1251 is then moved over tissue portions T1 and T2 to position the segment 1246 in engagement with the knotting element 1220' to effect a knot for the stitch segment between the end of the suture material and the distalmost knotting element to form a first stitch as shown in FIG. 35. The segment 1246 is pulled to tension or tighten the suture stitch to adjustably approximate the tissue portions T1 and T2, and the knotting element 1220' is closed by plastically deforming the opposed surfaces receiving the suture material segment 1246 to secure the thusly tightened suture stitch as described above. As noted above, the grasping instrument for deforming the knotting element can pass through the suturing instrument, or the suturing instrument can be constructed with jaws for deforming the knotting elements such that the number of instruments required can be reduced.

Figure 36:
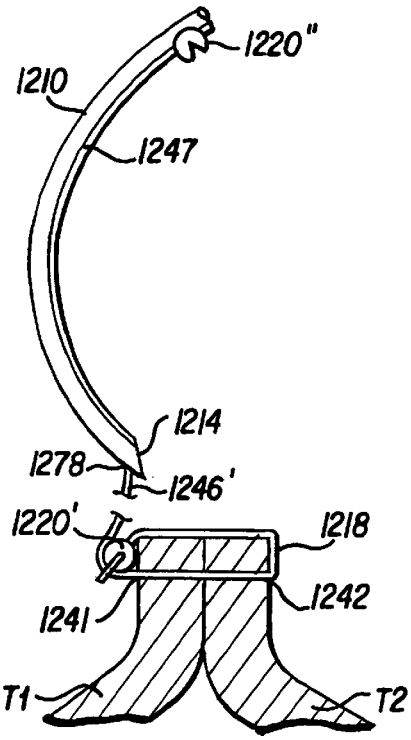

Once tying has been completed by deforming the knotting element to grasp the suture material, the needle 1210 is angled relative to the suture material to cause a new distal segment 1246' of suture material adjacent the distal end 1214 to enter the notch 1278 to be held thereby, and the suture material is cut or severed proximally of the knotting element 1220' to separate the thusly formed tightened suture stitch from the suture material held by needle 1210 as shown in FIG. 36. Once the stitch has been completed, the suturing apparatus is now ready to be used to form a second stitch without requiring removal of the suturing instrument from the body in that segment 1246' forms a new distal end or segment of suture material secured in notch 1478, and the next knotting element, schematically shown at 1220' in FIGS. 35 and 36 defines a new distalmost knotting element ready for use to tie the second stitch.

Modifications of suture supplies for use with the suturing instrument of FIG. 32 and in the procedure illustrated in FIGS. 34–36 are shown in FIGS. 37 and 38 and are exemplary of knotting elements that can be spaced at predetermined positions along a length of suture material for quickly tying knots with controlled tension where the knotting elements do not require plastic deformation or spring closure of opposed surfaces. In the modifications of FIG. 37, a suture supply includes a length of suture material 1518 having a plurality of knotting elements 1520, 1520a and 1520b secured thereto at spaced locations in the form of elastic rings normally disposed in a closed position wherein openings 1517 through the rings are collapsed or closed. Knotting element 1520 is formed by a single elastic ring having a peripheral edge secured to the suture material. Knotting element 1520a is formed by a pair of elastic rings secured at peripheral edges thereof to opposite sides of the suture material. Knotting element 1520b is formed of a pair of elastic rings having the sides thereof overlapping and secured to the suture material. In the modifications of FIG. 38, a suture supply includes a length of suture material 1618 having a plurality of knotting elements 1620, 1620a, 1620b, 1620c, 1620d and 1620e secured thereto at spaced locations. Knotting element 1620 is formed by a premade knot 1621 of the suture material defining a single loop 1622 while knotting element 1620a is similarly formed by a premade knot 1623 of the suture material to define an inner loop 1624 within a larger outer loop 1625. Knotting element 1620b is formed by passing the suture material through channels in a round member or ball 1626 to define an inner loop 1627 within a larger outer loop 1628, and knotting element 1620c is similarly formed by passing the suture material through channels in a ball 1629 to form a single loop 1630. In knotting element 1620d, a pair of double loops are formed by passing the suture material through a ball 1631 to form a first double loop of an inner loop 1632 and a larger outer loop 1633 and a second double loop of an inner loop 1634 and a larger outer loop 1635. Knotting element 1620e is formed of a ball 1636 made of a resilient, penetratable material, such as rubber or silicone, with the suture material passing through a bore or channel therethrough. The balls of knotting elements 1620b, 1620c and 1620d can be made of any medical grade absorbable or non-absorbable material or can be made of a resilient, penetrable material similar to ball 1636. While various different knotting elements are shown in FIGS. 37 and 38 carried by a single length of suture material, it will be appreciated that the knotting elements carried by a single length of suture material in accordance with the present invention can be identical or different dependent upon procedures to be performed.

The suture materials of FIGS. 37 and 38 can be received in a hollow needle with the knotting elements compressed within the needle to be maintained in a compressed or non-expanded position as shown in FIGS. 39 and 40, respectively. As shown in FIG. 39, suture material 1518 has a distal end 1546 held in a V-shaped notch 1578 adjacent a sharp distal end 1514 of a straight hollow needle 1510 having a lumen 1511 extending longitudinally therethrough. The elastic rings forming the knotting elements 1520, 1520a and 1520b are compressed within the lumen 1511 of needle 1510; and, once the needle is moved proximally and/or the distal end 1546 of suture material 1518 is pulled distally from the needle to an extent that a knotting element exits the open sharp end 1514 of the needle, the knotting element will expand to return to the position shown in FIG. 37. Similarly, as shown in FIG. 40, suture material 1618 has a distal end 1646 held in a V-shaped notch 1678 adjacent a sharp distal end 1614 of a straight hollow needle 1610 having a lumen 1611 extending longitudinally therethrough. The loops of the knotting elements 1620, 1620a, 1620b, 1620c and 1620d are compressed or folded within the lumen 1611 of needle 1610 and, the ball 1636, as well as the balls of knotting elements 1620b, 1620c and 1620d, can be of a size to fit within the lumen without compression or with compression. Once the needle is moved proximally and/or the distal end 1646 of suture material 1618 is pulled distally from the needle to an extent that a knotting element exits the open sharp end 1614 of the needle, the knotting element will expand to return to the position shown in FIG. 38. Accordingly, it will be appreciated that, upon extension of the knotting elements beyond the distal end of the needle, the knotting elements will expand, open or unfold to an expanded position wherein the cross-sectional size of the knotting element is preferably greater than the cross-sectional size of the needle.

Use of the suturing apparatus of FIGS. 39 and 40 is similar to that previously described with respect to FIGS. 34–36 except that, once the segment of the suture material secured in the notch at the distal end of the needle has exited tissue portion T2 and has been pulled to cause the distalmost knotting element to be disposed adjacent the tissue at the entry point, the needle is inserted through the distalmost knotting element to pass the segment of suture material therethrough. Where the knotting elements are made of elastic rings, the suture material will be passed through the openings 1517 of the rings; and, once the segment of suture material has been passed through the knotting element, the elastic rings will grip the segment of suture material tightly to effect a knot for the thusly formed suture stitch. Where the knotting elements are formed of loops, the suture material is passed in and out of the loops to effect tying; and, when a ball of resilient, penetrable material forms a part of the knotting element, the needle penetrates through the ball to pass the suture material therethrough such that the material of the ball resiliently grasps the suture material to form a knot or to assist forming a knot when used with loops. The suture material can be looped back and passed through the knotting elements several times such that multiple segments of the suture material are engaged by the knotting element for enhanced securement. Additionally, when the loops are not held tightly by the premade knots or balls, one or both of the suture material segments adjacent the loop formation can be pulled to close the loop formation around the suture material with the single and multiple loops providing redundant securement. The suture material can be looped back and passed through the loop formation several times before the loop formation is closed such that multiple segments of suture material are engaged by the knotting element. Where balls are utilized, the knotting elements can be movable along the length of the suture material to adjust the size of the stitch segments between the knotting elements.

The needle 1210 of the suturing instrument of FIG. 32 can have various configurations dependent upon tissue to be sutured including, for example, circular, arcuate, decreasing and increasing spiral, straight and bent configurations. When the needle is to be used with a suture supply having a length of suture material carrying a plurality of knotting elements, the needle is preferably hollow to have a lumen through which the suture material passes. Where the knotting elements can be compressed, the knotting elements can pass through the lumen along with the suture material, and no slot is required. Similarly, no slot is required in the needle where the knotting elements have a size to pass through the lumen, it being appreciated that in the latter case the stitch segments are joined at the knotting elements prior to tensioning the suture material to approximate tissue. Where the knotting elements have a size larger than the lumen and are not compressible, a longitudinal slot in the needle is provided in communication with the lumen to allow the knotting elements to pass externally along the needle while the suture material passes internally through the lumen of the needle.

FIG. 41 illustrates at 2020 a modification of a knotting element according to the present invention, the knotting element 2020 including opposed hinge components 2090 and 2091. Hinge component 2090 includes a hollow cylinder 2092 joined to a wing 2022 by spaced legs 2093 extending from cylinder 2092. Wing 2022 has an inner surface formed with a longitudinal groove 2029, and a plurality of teeth are disposed along the inner surface of wing 2022. Hinge component 2091 includes an annular or ring member 2094 rotatably disposed on cylinder 2092 between legs 2093 and joined to a wing 2024 by a leg 2095 extending from ring 2094. Cylinder 2092 and ring 2094 are rotatably positioned relative to one another to be in an open position such that an inner surface of wing 2022 is opposed to and spaced from an inner surface of 2024 to define a space or opening therebetween for receiving a segment of suture material. The inner surface of wing 2024 has a longitudinal tongue 2021 thereon for being received in groove 2029 when the knotting element is moved to a closed position, and a plurality of teeth are disposed along the inner surface of wing 2024. A tooth 2096 protrudes inwardly from wing 2022 between legs 2093 to be in engagement with one of a plurality of grooves or teeth 2097 disposed along an outer surface of ring 2094. The knotting element 2020 can be secured to a first segment of a length of suture material in many various ways such as by arranging the suture material to extend through cylinder 2092 with a friction fit.

In use, a second segment of the suture material is positioned between opposed wings 2022 and 2024 to form a suture stitch, and the knotting element is moved to the closed position by rotating components 2090 and 2091 to move the inner surfaces of wings 2022 and 2024 toward one another. With the inner surfaces in abutment, tongue 2021 will be received in groove 2029 to lock the knotting element in the closed position, and the teeth on the inner surfaces will grip the suture material. The tooth 2096 and grooves 2097 provide a one-way action mechanism permitting the knotting element to be moved toward the closed position and preventing movement of the knotting element back toward the open position once the knotting element has been moved toward the closed position.

Figure 42:
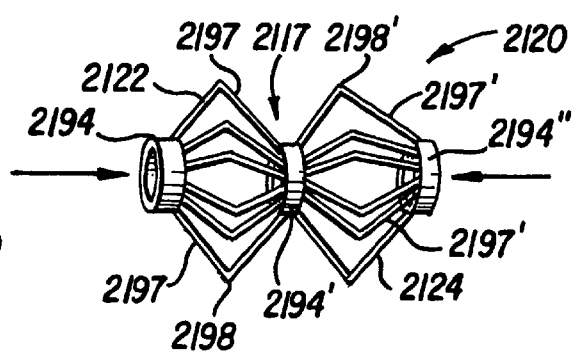
FIG. 42 is a perspective view of a further knotting element in accordance with the present invention.

Another modification of a knotting element according to the present invention is shown in FIG. 42 wherein the knotting element 2120 includes opposing portions 2122 and 2124 formed of a plurality of arms 2197 hinged at joints, hinges or pivots 2198. Arms 2197 for opposing portion 2022 have distal segments pivotally secured to an outer ring 2194 and proximal segments pivotally secured to an inner ring 2194', smaller than outer ring 2194, with the distal and proximal segments pivotally connected to one another at joints 2198 between rings 2194 and 2194'. Arms 2197' for opposing portion 2024 have distal segments pivotally secured to inner ring 2194' and proximal segments pivotally secured to an outer ring 2194", larger than inner ring 2194', with the distal and proximal segments pivotally connected to one another at joints 2198' between the rings 2194' and 2194". Rings 2194, 2194' and 2194" are arranged in longitudinal alignment to allow the inner ring to enter the outer rings when the knotting element is moved to a closed position. The arms can be made of a flexible or resilient material to be normally disposed in an open position as shown wherein a space 2117 is defined between opposing portions 2122 and 2124 for receiving a segment of suture material which can be attached to knotting element 2120 in many various ways including being frictionally received in the rings.

In use, a segment of suture material is positioned between opposing portions 2122 and 2124 to form a suture stitch, and the opposing portions are moved toward one another as shown by the arrows in FIG. 42 causing the knotting element to be moved to a closed or collapsed position wherein the distal and proximal segments of arms 2197 and 2197' are brought toward one another and ring 2194' enters rings 2194 and 2194" to be held thereby. Each of the rings can be designed to be arranged concentrically with one another in the closed position, and various locking structure can be provided on the rings to lock the knotting element in the closed position.

While the present invention has the advantage of utilizing conventional filamentous suture materials, particular advantages can be obtained where the suture material is stretchable, for example in microsurgery, and where, as shown in FIG. 43, a length of hollow suture material 2218 is used having a lumen 2219 therein which can contain substances, such as medicaments, that can leach out of the suture material through microholes 2221 communicating with the lumen to treat tissue in which the suture material is embedded.

Figure 44:
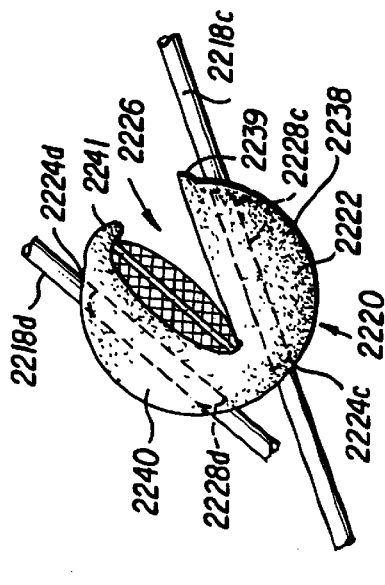
FIGS. 44 and 45 are broken perspective views illustrating various attachment sites for knotting elements according to the present invention.
Figure 45:
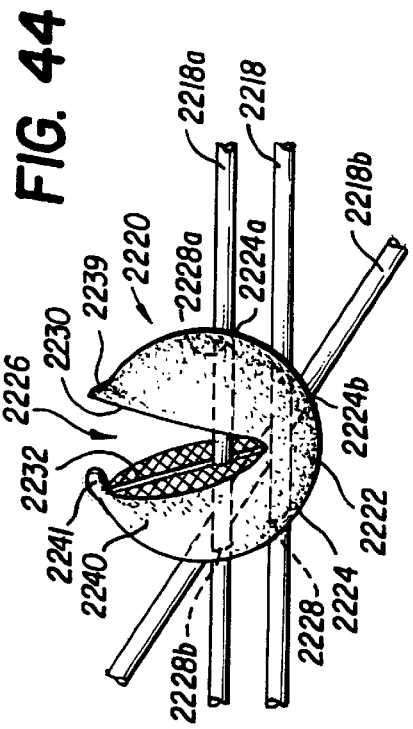

The site of attachment of suture material to knotting elements in accordance with the present invention is desirably varied to maximize the ease of placing a segment of suture material between the opposing surfaces at the grasping site for specific procedures. Additionally, it can be desirable to attach a plurality of lengths of suture material to a single knotting element, as exemplified in FIG. 11, or to attach a knotting element having a plurality of grasping sites, as exemplified in FIGS. 14 and 15, at a specific location along a length of suture material. Further examples of attachment of lengths of suture material to knotting elements in accordance with the present invention are shown in FIGS. 44 and 45 wherein a knotting element 2220, similar to the knotting elements of FIG. 1, has a spherical body 2222 with a grasping site 2226 defined between opposed surfaces 2230 and 2232 of jaws 2238 and 2240, respectively. Jaw 2238 terminates at a locking protrusion 2239, and jaw 2240 terminates at a locking lip 2241 having a configuration complementary to the configuration of protrusion 2239 whereby the jaws can be locked together as well as being plastically deformed to grasp suture material. As shown in FIG. 44, attachment sites 2224, 2224a and 2224b can be formed by bores or passages 2228, 2228a and 2228b extending substantially transversely to the jaws near the periphery of the body, extending substantially transversely to and through the jaws and extending angularly relative to the jaws, respectively, permitting one or more of the knotting elements to be carried by one or more lengths of suture material 2218, 2218a and 2218b in a fixed or slidable manner. FIG. 45 illustrates attachment sites 2224c and 2224d formed of bores 2228c and 2228d extending in parallel with jaws 2238 and 2240, respectively, to permit one or more of the knotting elements to be carried by one or more lengths of suture material 2218c and 2218d in a fixed or slidable manner. The knotting elements or passages through the body of the knotting elements can be straight or curved dependent upon the resistance to sliding movement of the knotting elements desired, and an arrangement of successive curves can be used to provide a serpentine configuration.

Figure 46:
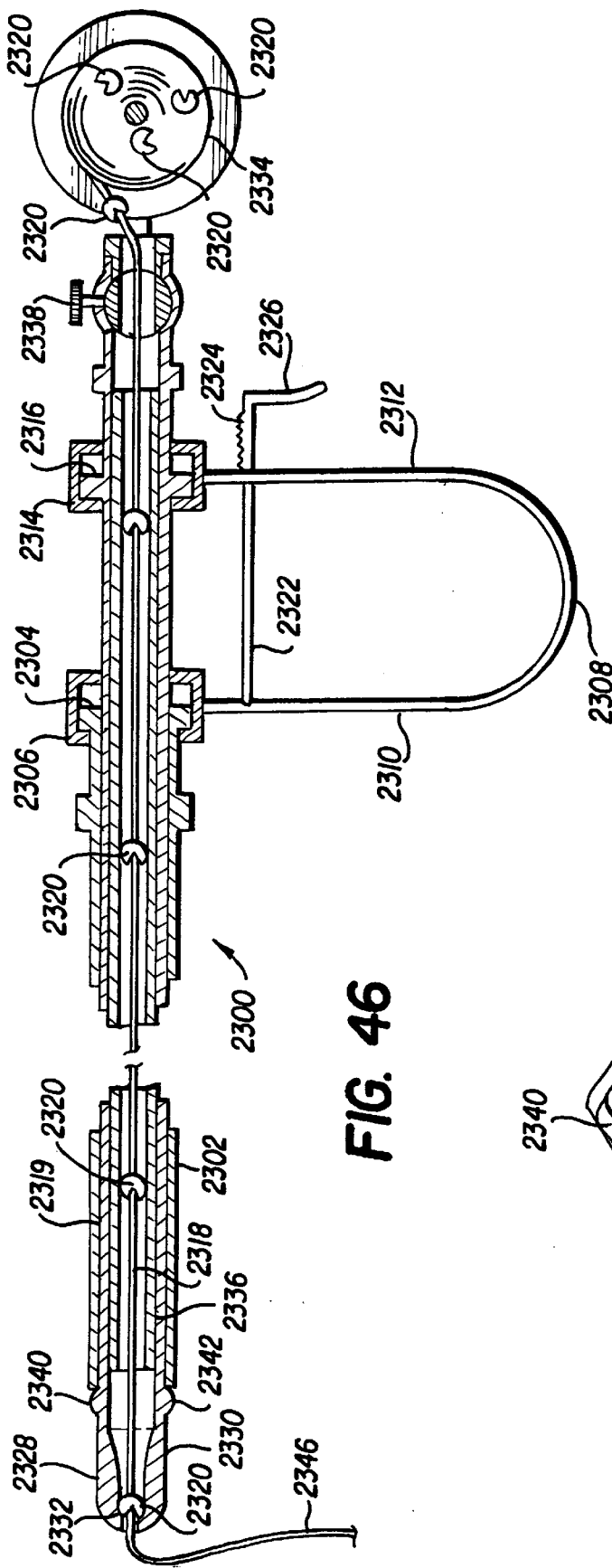
FIG. 46 is a sectional side view of a suturing instrument according to the present invention particularly useful in forming free tie stitches.
Figure 47:
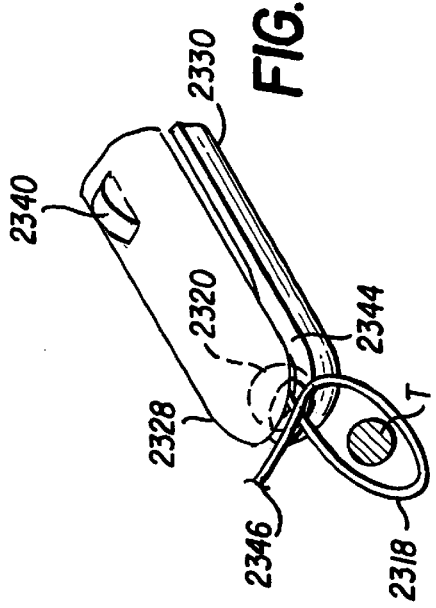
FIG. 47 is a broken perspective view of the distal end of the suturing instrument of FIG. 46 during use.

An instrument 2300 according to the present invention for applying a plurality of free-tie stitches is shown in FIGS. 46 and 47 and includes an outer tubular member 2302 having a proximal end carrying a flange 2304 rotatably received in an annular collar 2306 secured to a handle 2308 at the proximal end of the instrument. The handle 2308 is formed of spring biased legs 2310 and 2312 with leg 2310 secured to collar 2306 and leg 2312 secured to an annular collar 2314 rotatably receiving a flange 2316 on a proximal portion of a middle tubular member 2319 slidably received within outer tubular member 2302. An arm or cross bar 2322 has an end fixed to leg 2310 of handle 2308 and carries ratchet teeth 2324 at a position to be engaged by teeth, not shown, carried by leg 2312, the cross bar 2322 terminating at a trigger 2326. The middle tubular member 2319 terminates distally at a pair of opposed jaws 2328 and 2330 having inner surfaces configured to form a recess 2332 having a configuration for receiving knotting elements schematically shown at 2320. The knotting elements 2320 have attachment sites fixed to or slidably receiving a length of suture material 2318, and a suture supply composed of the knotting elements and the suture material can be provided on a wound spool as shown at 2334. An inner tubular member 2336 can be separate from or attached to spool 2334 such that a suture supply cartridge can be formed of the spool 2334 with the suture material and knotting elements wound thereon or the spool 2334 in combination with the inner tubular member 2336. The suture material and knotting elements pass through a stopcock-type valve 2338 at the proximal end of the instrument for use in limiting movement of the suture material as well as operation as a stopcock for passage of fluids or instruments through the central channel through the instrument. The jaws 2328 and 2330 carry camming protrusions 2340 and 2342, respectively, and the jaws are biased to have an open position when middle member 2319 is moved distally relative to outer member 2302. The legs of handle 2308 are spring biased such that jaws 2328 and 2330 are normally in a rest position with a gap 2344 therebetween, and squeezing legs 2310 and 2312 together.causes the jaws to open while squeezing trigger 2326 and leg 2312 together forces jaws 2328 and 2330 further together to deform a knotting element therein with the ratchet teeth 2324 holding the jaws in the deforming position.

In use, the instrument is positioned in the surgical field, such as through a portal sleeve for endoscopic procedures, and a distal end 2346 of the suture material 2318 is pulled to position a distalmost knotting element 2320 in the recess 2332 in the jaws at the distal end of the instrument, the jaws flexing slightly to allow the knotting element to be received in the recess. The exposed suture material is then manipulated around tissue to be sutured or tied and then placed in the mouth or grasping site of the knotting element by aligning the suture material with the gap 2344 disposed between the jaws 2328 and 2330 as shown in FIG. 47 such that tissue T is encircled by the suture material. The suture material can then be pulled through the grasping site of the knotting element to tighten the stitch formed thereby to a desired tension at which time leg 2312 and trigger 2326 of the handle are squeezed moving the distal end of outer tubular member 2302 over protrusions 2340 and 2342 to compress jaws 2328 and 2330 to deform the jaws of the knotting element to grasp the suture material thereby forming a knot. Thereafter, legs 2310 and 2312 of handle 2308 are squeezed causing the jaws 2328 and 2330 to open and release the knotting element. The legs 2310 and 2312 are then released allowing the jaws to return to the rest position as shown in FIG. 46, and the instrument is moved proximally causing suture material to exit through the distal tip of the jaws of the instrument. In this position, the suture material can be cut adjacent the deformed knotting element, and the instrument can be used to form a subsequent free tie stitch.

Figure 48:
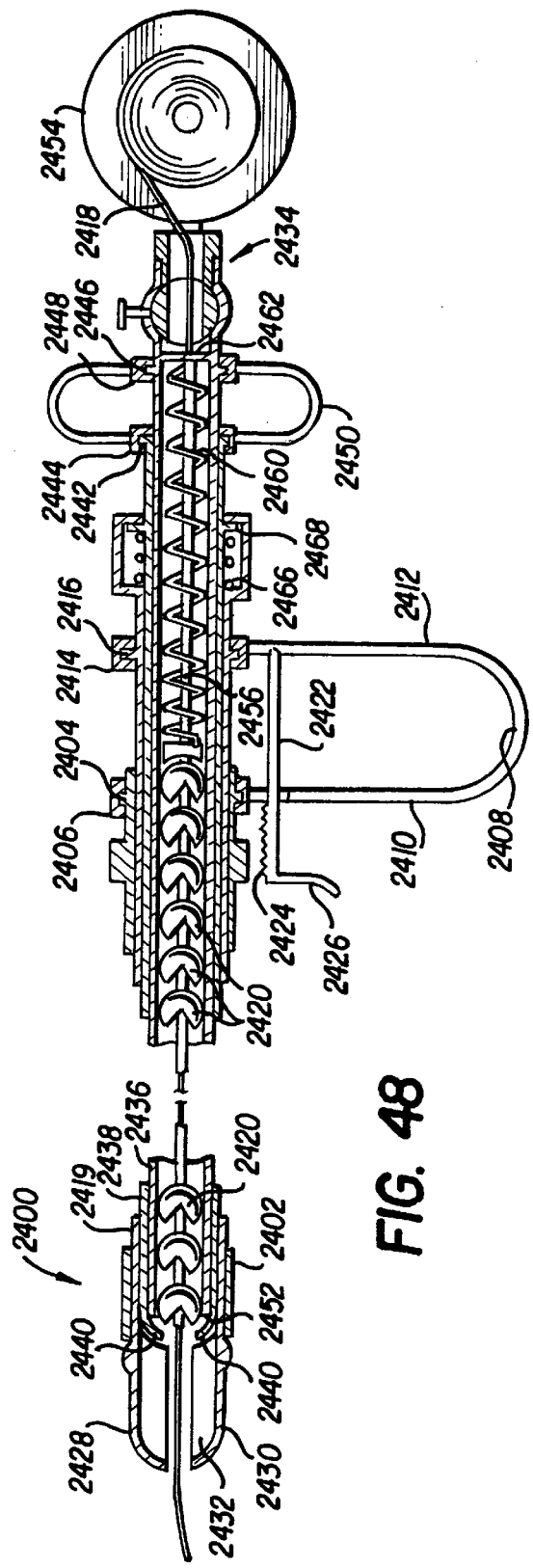
FIG. 48 is a sectional side view of another suturing instrument according to the present invention particularly useful in forming free tie stitches.

An instrument 2400 according to the present invention for applying a plurality of free-tie stitches is shown in FIG. 48 with the primary difference between instruments 2300 and 2400 being that, in the instrument 2400, the suture material is wound on a spool while the knotting elements are supplied in a cartridge with the suture material running freely therethrough. Instrument 2400 includes an outer tubular member 2402 having a proximal end carrying a flange 2404 rotatably received in an annular collar 2406 secured to a handle 2408 at the proximal end of the instrument. The handle 2408 is formed of spring biased legs 2410 and 2412 with leg 2410 secured to collar 2406 and leg 2412 secured to an annular collar 2414 rotatably receiving a flange 2416 on a proximal portion of a middle tubular member 2419 slidably received within outer tubular member 2402. An arm or cross-bar 2422 has an end fixed to leg 2412 of handle 2408 and carries ratchet teeth 2424 at a position to be engaged by teeth, not shown, carried by leg 2410, the cross bar 2422 terminating at a trigger 2426. The middle tubular member 2419 terminates distally at a pair of opposed jaws 2428 and 2430 having inner surfaces configured to form a recess 2432 having a configuration for receiving knotting elements schematically shown at 2420.

The knotting elements 2420 are provided in a cartridge 2434, as shown in FIG. 49, the cartridge including an inner member 2436 slidably telescoping within an outer member 2438, and the outer member has flaps 2440 extending radially inwardly to cover the distal end of the inner member 2436. The outer cartridge member 2438 carries a flange 2442 at a proximal end thereof received within an annular collar 2444, and inner cartridge member 2436 carries a flange 2446 at a proximal end thereof received within an annular collar 2448. A handle formed of spring biased U-shaped members 2450 is attached to the collars 2444 and 2448 such that, in a rest position, a distal end 2452 of the inner cartridge member 2436 is adjacent the flaps 2440 on the outer cartridge member 2438. A stopcock-type valve 2453 is disposed between handle 2450 and a spool 2454 of suture material 2418 to control the movement of the suture material. A central tube 2456 extends from spool 2454 through the cartridge to the distal end thereof, and a plurality of knotting elements 2420 are disposed within inner cartridge member 2436 on the tube 2456 and are biased toward the distal end of the cartridge by a pusher 2458 spring biased distally via a coiled compression spring 2460 mounted between the pusher and a fixed washer 2462 having a central opening receiving the central tube 2456. The suture material 2418 can be pulled through the instrument and knotting elements from the distal end or can be driven through the instrument by rotating spool 2454 or friction rollers associated therewith, not shown.

The cartridge 2434 is operated by the instrument 2400 to eject individual knotting elements similar to conventional multiple clip appliers, and any conventional mechanism can be utilized to eject the knotting elements from the cartridge into the jaws 2428 and 2430. In the particular embodiment illustrated, the distalmost knotting element 2420 is ejected into the recess 2432 formed by jaws 2428 and 2430 by squeezing handle 2450 which causes inner cartridge member 2436 to move distally thereby pushing flaps 2440 away from the distal end of the cartridge allowing the distalmost knotting element to be ejected into the jaws. Any conventional mechanism can be utilized to assure that only a single knotting element is ejected each time the handle 2450 is squeezed. In the illustrated embodiment, the cartridge is moved distally against the bias of a spring 2466 mounted in compression between the proximal end of middle tubular member 2419 and a flange 2468 carried by outer cartridge member 2438 such that the distal end of the cartridge moves distally to a position where only a single knotting element 2420 can be ejected since the space remaining in recess 2432 is insufficient to permit the next knotting element to be ejected.

The knotting elements can have any configuration discussed above and will be oriented as desired for particular procedures such that the mouth defined by the grasping site is properly oriented. To this end, the central tube 2456, or in the alternative the suture material 2418 without utilizing the tube 2456, can pass through any desired attachment site in the knotting elements to produce a desired orientation.

In use, the jaws 2428 and 2430 can be opened by squeezing handle 2408, and the knotting elements can be deformed to form a knot after a free-tie stitch has been completed by squeezing trigger 2426 and leg 2410 in the manner described above with respect to instrument 2300. The cartridge 2434 can be replaced within the instrument by removing the flange 2466 from the middle tubular member such that the cartridges can be disposable and the instrument reusable.

Instrument 2400 can be modified, as shown in FIGS. 50 and 51, to carry a hollow needle 2510, the needle being disposed on the distal end of the outer tubular member 2402. As previously discussed, the needle can have a V-shaped notch in the distal end thereof for carrying suture material along therewith or suture material can be forced or pushed through the hollow needle. Additionally, dependent upon the size and configuration of the knotting elements, the needle can have a slot therein as shown at 2511. Use of the instrument of FIG. 50 permits the formation of a plurality of stitches in a manner similar to that described with respect to FIGS. 34 through 36 in that, after the distal end of the suture material is grasped at the exit point of tissue being sutured, the jaws 2428 and 2430 can be opened and the needle moved proximally such that the suture material passes through the needle and the needle passes proximally beyond the knotting element held within the jaws 2428 and 2430. With the jaws open, the knotting element will move beyond the distal ends of the jaws; and, thereafter, the jaws can be closed to be used to push the knotting element to a desired position and/or to recapture the knotting element. Once the suture material is inserted into the grasping site in the knotting element, the jaws can be compressed to secure the suture material in the grasping site thereby completing an adjustably tensionable stitch. Thereafter, the suture material is cut and an additional stitch can be made in the same manner as described above with respect to instrument 2400.

Where only a single stitch is desired to be made, an instrument carrying suture apparatus in accordance with the present invention, as shown in FIG. 51, can be utilized. The instrument 2600 is formed of a barrel 2602 having a socket 2604 in a distal end thereof adapted to receive a complementary configured male member 2606 on the proximal end of a needle 2610 having suture material 2618 attached adjacent a distal end 2614 of the needle. The suture material 2618 carries a single knotting element, schematically shown at 2620, disposed within barrel 2602. The type of suture apparatus including the configuration of the suture material and the configuration of the knotting element can be varied in accordance with the procedure to be performed by merely attaching the desired suture apparatus to the barrel 2604 by inserting the proximal end of the needle in socket 2604. Accordingly, needles having hook-shaped, curved, straight, circular, spiral, bent and other configurations can be utilized with instrument 2600. Preferably, a tubular sheath 2616 is movably disposed over barrel 2602 to allow the sheath to be disposed over the needle 2610 during insertion of the instrument through a portal sleeve. Additionally, the instrument 2600 preferably carries an electrosurgical connector 2622, and the barrel 2602 has a flange 2624 at the proximal end thereof rotatably mounted in a handle 2626 to allow rotation of the barrel relative to the handle with a thumb lock 2628 provided to lock the barrel in a desired rotational orientation relative to the handle.

The needles utilized in the present invention can have any suitable configuration, such as straight, curved or bent with a sharp distal end and/or a sharp proximal end. The suture material can be coupled to the needle at any desirable location along the body of the needle or can extend entirely or partly through the needle. The suture material can be formed of various materials including bioabsorbable materials, non-bioabsorbable materials, stretchable materials and/or non-stretchable materials. Preferably, the suture material is formed as a length of filamentous suture material familiar to surgeons, and the suture material can be solid or hollow with holes in the suture material for supplying substances such as medicaments. One or more than one length of suture material can be coupled with a needle at different attachment positions along or within the body of the needle. The length of the suture material can be selected to correspond to the size of a suture stitch desired to be formed; and, where more than one knotting element is secured to the suture material, stitch segments can be defined between two knotting elements.

The knotting elements can be made of various materials including bioabsorbable, non-bioabsorbable and compressible materials. With the use of rubber-like materials, the needle can be used to penetrate the knotting elements to pass a segment of the suture material therethrough. The knotting elements have one or more attachment sites secured to one or more segments of suture material and one or more grasping sites for grasping other segments of the suture material to effect a knot after the suture material has been tensioned and engaged by the knotting element. The manner in which the knotting elements are carried by the suture material and the orientation of the knotting elements at the attachment sites allows the knotting elements to be optimally positioned in accordance with procedural use. The knotting elements are preferably plastically deformable to be movable between a first position for receiving a segment of the suture material and a second position for grasping the segment of suture material to effect the knot for a suture apparatus including a needle and a single knotting element carried by a length of suture material; however, in a suture supply according to the present invention the knotting elements can have any deformable as well as non-deformable structure to engage spaced segments of suture material. The knotting elements can have one or more filamentous tails extending from bodies thereof to facilitate manipulating of the knotting elements.

The instruments of FIGS. 32, 46, 48 and 50 are particularly advantageous for forming multiple suture and free-tie stitches in accordance with the present invention without withdrawing the isntruments from a surgical site and also since the instruments can be used with suture supplies in pre-packaged or cartridge form such that multiple suture supply packages or cartridges can be provided for use with a single instrument. Furthermore, the suture supplies can be provided with variously configured and oriented knotting elements according to the present invention such that the instruments can be used in various procedures. The features of the knotting elements described above can be combined in individual knotting elements as desired. Accordingly, any of the knotting elements can have one or more manipulating tails extending therefrom at any location and any of the knotting elements can be carried by more than one length of suture material or can have multiple grasping sites to grasp more than one length of suture material or a single length of suture material at different segments thereof.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A suturing apparatus comprising:

a needle having a sharp distal end for penetrating anatomical tissue;

a length of filamentous suture material having a first end received by said needle and a second end; and a knotting element formed at said second end of said suture material, said knotting element being formed by a premade knot of said suture material and including a first loop having segments engaged with said premade knot and a second loop having segments engaged with said premade knot for insertion of said needle through said first loop and said second loop to pass said suture material through said knotting element to permit tying of a knot.

2. A suturing apparatus as recited in claim 1 wherein said first loop is smaller than said second loop.

* * * * *